US010071381B2

(12) United States Patent
Welch et al.

(10) Patent No.: US 10,071,381 B2
(45) Date of Patent: Sep. 11, 2018

(54) METHOD AND APPARATUS FOR HANDLING BLOOD FOR TESTING

(71) Applicant: Neoteryx, LLC., Torrance, CA (US)

(72) Inventors: Emmet Welch, Torrance, CA (US); Gene Zamba, Torrance, CA (US); Allen Bischofberger, Torrance, CA (US); Stuart Kushon, Torrance, CA (US)

(73) Assignee: Neoteryx, LLC., Torrance, CA (US)

( * ) Notice: Subject to any disclaimer, the term of this patent is extended or adjusted under 35 U.S.C. 154(b) by 4 days.

(21) Appl. No.: 15/130,373

(22) Filed: Apr. 15, 2016

(65) Prior Publication Data

US 2017/0043346 A1 Feb. 16, 2017

Related U.S. Application Data

(60) Provisional application No. 62/149,415, filed on Apr. 17, 2015.

(51) Int. Cl.
*B01L 9/06* (2006.01)
*B01L 9/00* (2006.01)
(Continued)

(52) U.S. Cl.
CPC ................ *B01L 9/543* (2013.01); *A61B 5/15* (2013.01); *A61B 5/150305* (2013.01); *B01L 3/50* (2013.01); *B01L 3/5085* (2013.01); *B01L 9/06* (2013.01); *B01L 9/547* (2013.01); *B65D 25/108* (2013.01); *B65D 25/24* (2013.01); *G01N 35/00* (2013.01); *B01L 2200/025* (2013.01);
(Continued)

(58) Field of Classification Search
CPC ........ G01N 2001/028; B01L 9/06; B01L 9/54; B01L 9/543; B01L 3/5085; B01L 3/50853
See application file for complete search history.

(56) References Cited

U.S. PATENT DOCUMENTS 3,164,279 A 1/1965 Towns
3,452,601 A 7/1969 Mogayzel et al.
(Continued)

FOREIGN PATENT DOCUMENTS

EP 0283613 A2 9/1988
EP 0940678 A1 9/1999
(Continued)

OTHER PUBLICATIONS

International Search Report for PCT/US12/63586 filed Nov. 5, 2012 for applicant James Rudge.
(Continued)

*Primary Examiner* — Jan Ludlow
(74) *Attorney, Agent, or Firm* — Stetina Brunda Garred & Brucker; Lowell Anderson

(57) ABSTRACT

A holder rack has an array of tubular slots that cooperate with a holder to position an absorbent tip of the holder at a predetermined location. The racks fit over well plates to position each absorbent tip adjacent the bottom of a different well in the well plate to extract dried samples from the absorbent tips. The holders are transported in containers having a frame to receive the holders and a lid to keep them in the container. The absorbent tips can extend through a cap to dry, with the cap connected to the holder to enclose the absorbent tips for transport.

16 Claims, 19 Drawing Sheets

(51) Int. Cl.
*A61B 5/15* (2006.01)
*B01L 3/00* (2006.01)
*B65D 25/10* (2006.01)
*B65D 25/24* (2006.01)
*G01N 35/00* (2006.01)

(52) U.S. Cl.
CPC ..... *B01L 2200/185* (2013.01); *B01L 2300/02* (2013.01); *B01L 2300/021* (2013.01); *B01L 2300/041* (2013.01); *B01L 2300/042* (2013.01); *B01L 2300/0609* (2013.01); *B01L 2300/069* (2013.01); *B01L 2300/0829* (2013.01); *B01L 2300/0832* (2013.01); *B01L 2300/0838* (2013.01); *B01L 2300/0851* (2013.01); *B01L 2400/0406* (2013.01)

(56) References Cited

U.S. PATENT DOCUMENTS

| | | |
|---|---|---|
| 3,620,677 A | 11/1971 | Morison |
| 4,175,008 A | 11/1979 | White |
| 4,635,488 A | 1/1987 | Kremer |
| 4,648,408 A | 3/1987 | Hutcheson et al. |
| 4,678,757 A | 7/1987 | Rapkin |
| 5,009,316 A * | 4/1991 | Klein ............... B01L 9/06 206/443 |
| 5,011,779 A | 4/1991 | Maimon |
| 5,014,718 A | 5/1991 | Mitchen |
| 5,057,282 A | 10/1991 | Linder |
| 5,064,541 A | 11/1991 | Jeng et al. |
| 5,078,968 A | 1/1992 | Nason |
| 5,324,482 A | 6/1994 | Scaramella et al. |
| 5,418,143 A | 5/1995 | Zweig |
| 5,427,953 A | 6/1995 | Yee |
| 5,494,646 A | 2/1996 | Seymour |
| 5,830,154 A | 11/1998 | Goldstein et al. |
| 5,895,704 A | 4/1999 | Lerch et al. |
| 5,922,614 A | 7/1999 | Cesarczyk |
| 6,036,659 A | 3/2000 | Ray et al. |
| 6,060,022 A | 5/2000 | Pang et al. |
| 6,309,887 B1 | 10/2001 | Ray |
| 6,383,804 B1 | 5/2002 | Ward, Jr. et al. |
| 6,524,533 B1 | 2/2003 | Tyrrell |
| 7,141,213 B1 | 11/2006 | Pang et al. |
| 7,374,723 B2 | 5/2008 | Wuske et al. |
| 7,611,670 B2 | 11/2009 | Wandell et al. |
| 7,686,681 B2 | 3/2010 | Di Luccio et al. |
| 8,038,942 B2 | 10/2011 | Pang et al. |
| 8,141,717 B2 | 3/2012 | Wingo et al. |
| 8,852,122 B2 | 10/2014 | Mao et al. |
| 8,920,339 B2 | 12/2014 | Mao et al. |
| 8,940,252 B2 | 1/2015 | Ziegler |
| 2002/0108917 A1 * | 8/2002 | Maruyama ............... B01L 9/06 211/74 |
| 2003/0045814 A1 | 3/2003 | Sangha |
| 2003/0119202 A1 | 6/2003 | Kaylor et al. |
| 2004/0126283 A1 | 7/2004 | Backes et al. |
| 2005/0009200 A1 | 1/2005 | Guo et al. |
| 2005/0227269 A1 | 10/2005 | Lloyd, Jr. et al. |
| 2005/0252820 A1 | 11/2005 | Sanchez-Felix et al. |
| 2006/0229530 A1 | 10/2006 | Hosoda et al. |
| 2008/0060424 A1 | 3/2008 | Babic et al. |
| 2008/0249487 A1 | 10/2008 | Engvall |
| 2011/0004122 A1 | 1/2011 | Sangha |
| 2011/0224579 A1 | 9/2011 | Maas et al. |
| 2011/0300620 A1 | 12/2011 | Belz et al. |
| 2013/0116597 A1 | 5/2013 | Rudge et al. |
| 2014/0018701 A1 | 1/2014 | Mao et al. |

FOREIGN PATENT DOCUMENTS

| | | |
|---|---|---|
| EP | 1712180 A1 | 10/2006 |
| EP | 2128617 A1 | 12/2009 |
| JP | 63215939 | 9/1988 |
| JP | 05503230 | 6/1993 |
| JP | 05187976 | 7/1993 |
| JP | 09190796 | 7/1997 |
| JP | 11076213 | 3/1999 |
| JP | 2005017280 | 1/2005 |
| JP | 2005022316 | 3/2005 |
| JP | 2005283366 | 10/2005 |
| JP | 2008521019 | 6/2008 |
| JP | 2010127059 | 11/2010 |
| WO | 199502996 A1 | 2/1995 |
| WO | 2005018803 A1 | 3/2005 |
| WO | 2010114976 A1 | 10/2010 |
| WO | 2012145379 A1 | 10/2012 |
| WO | 2012145390 A1 | 10/2012 |

OTHER PUBLICATIONS

Patent Search Report for Method and Apparatus for Handling Blood for Testing, in the name of Emmet Welch et al., PCT/US2016/027887, filed Apr. 15, 2016.

* cited by examiner

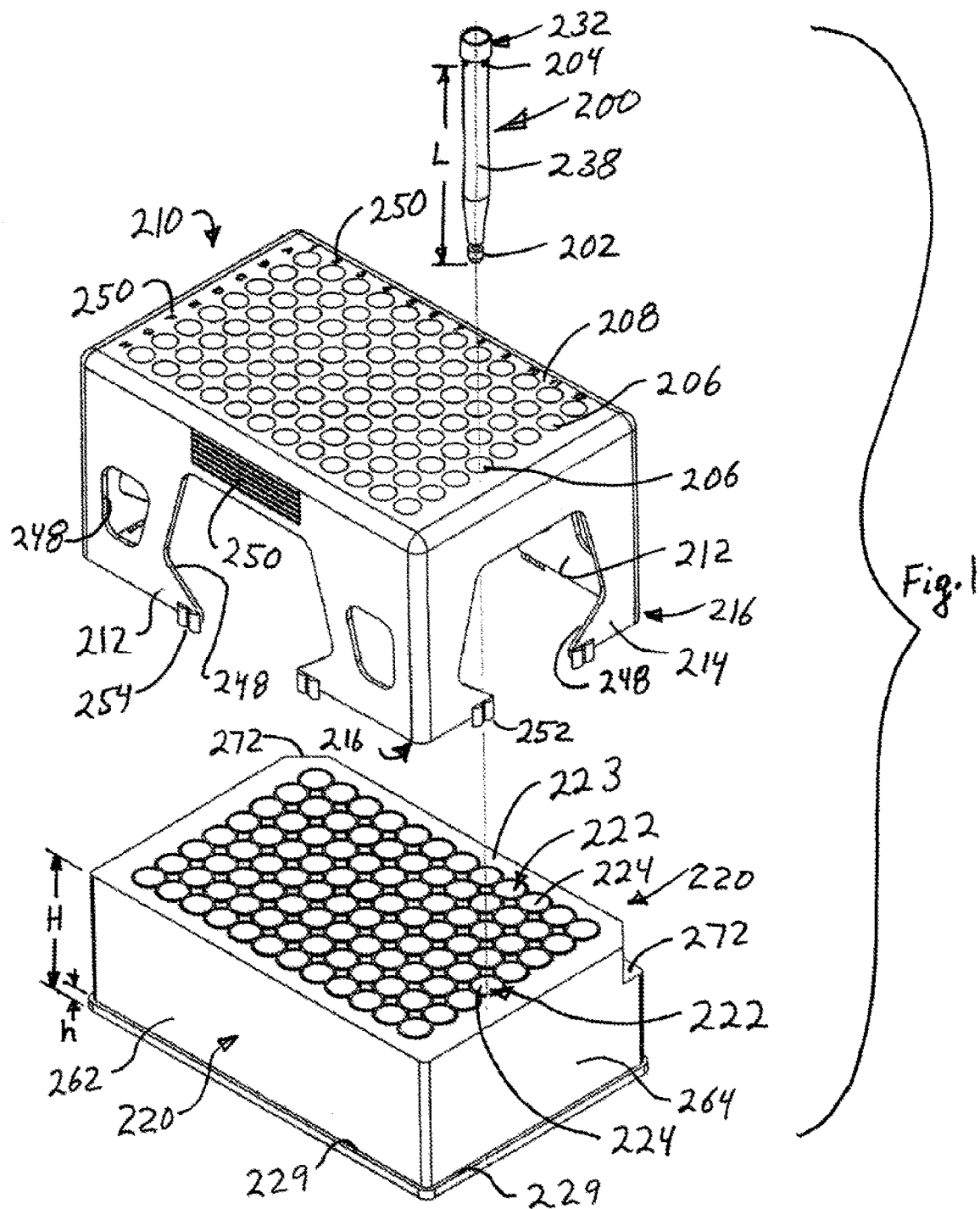

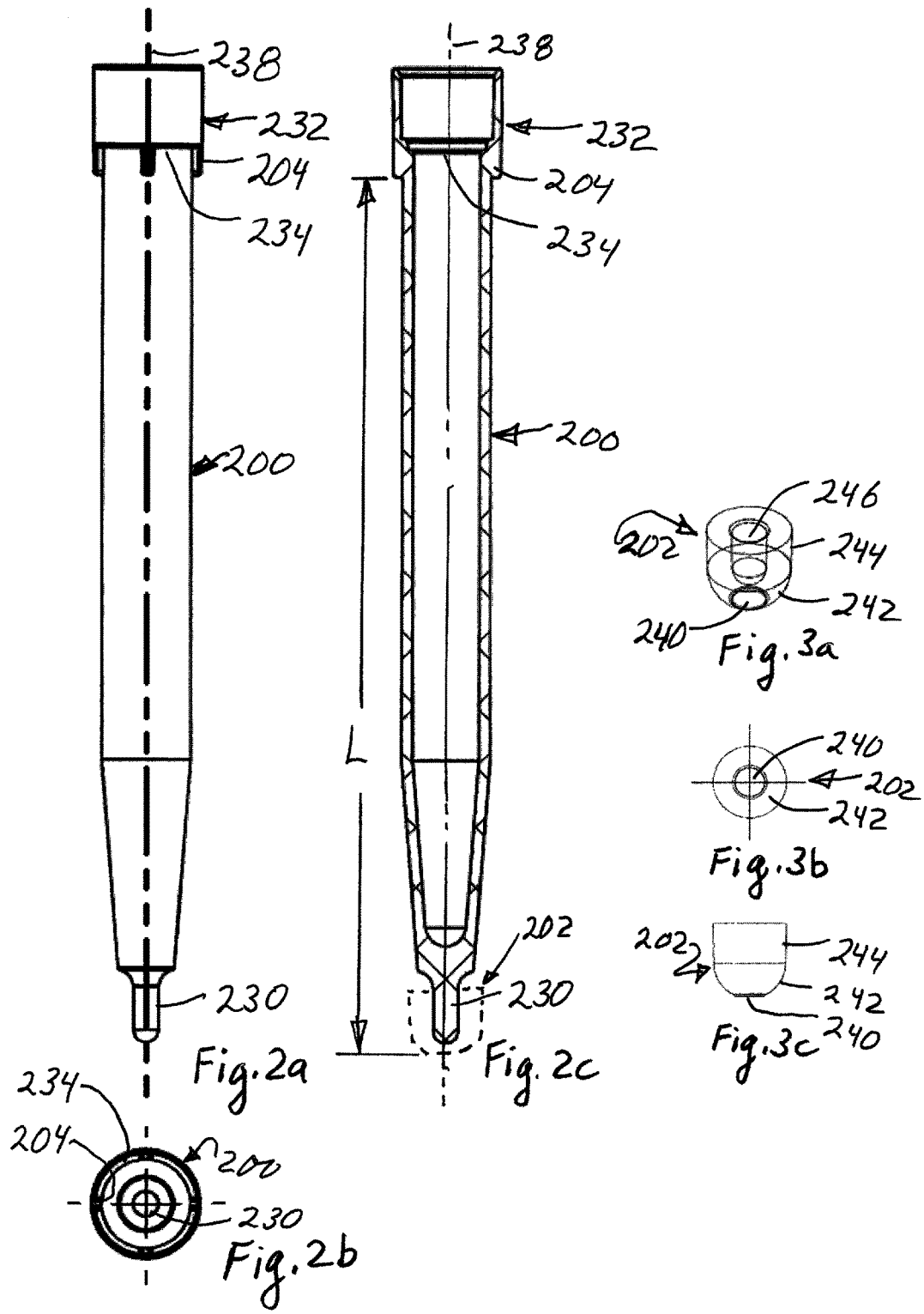

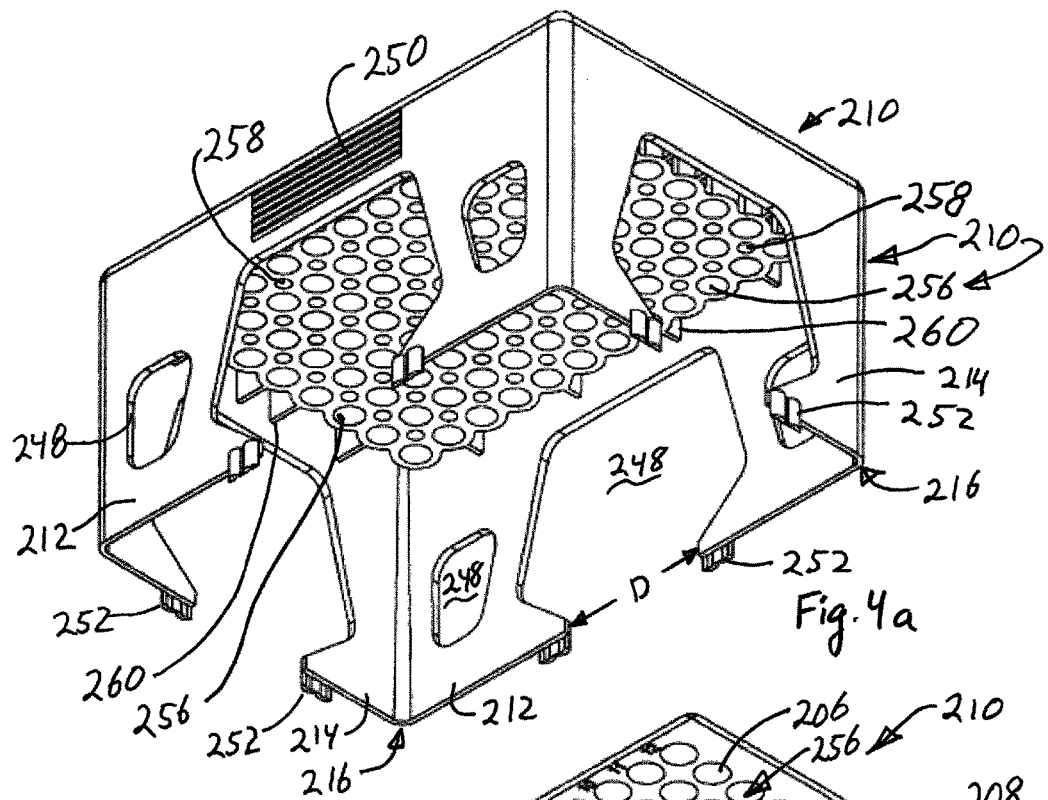
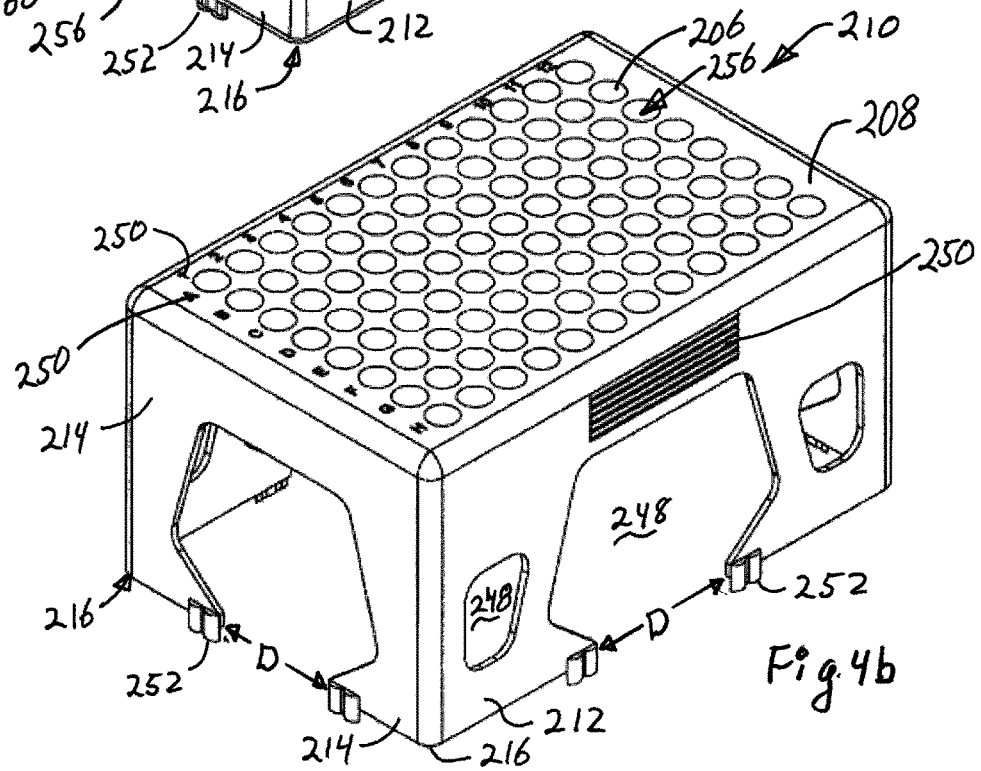

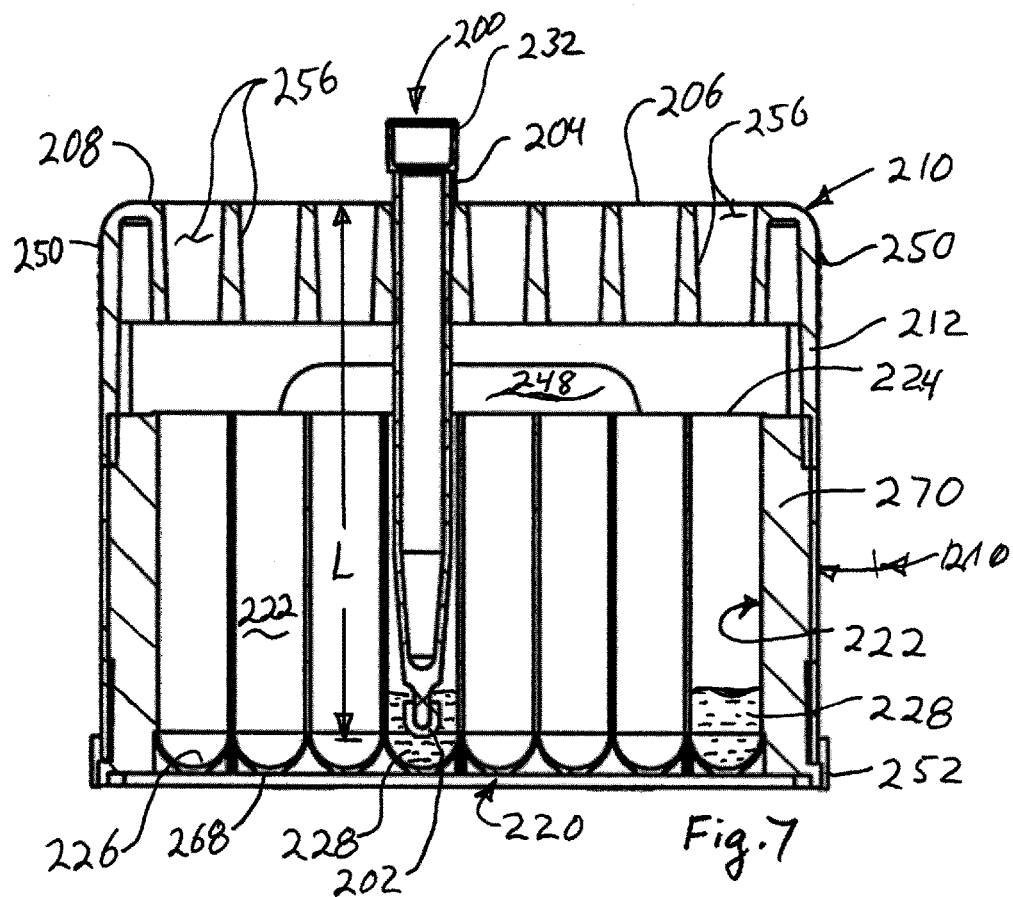
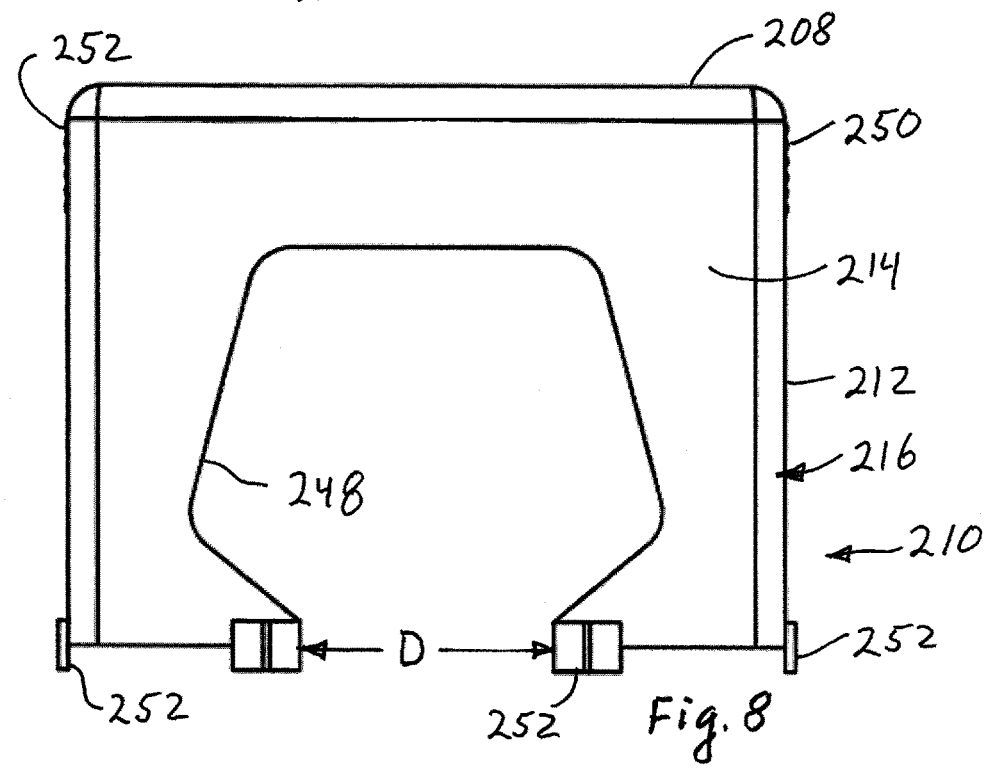

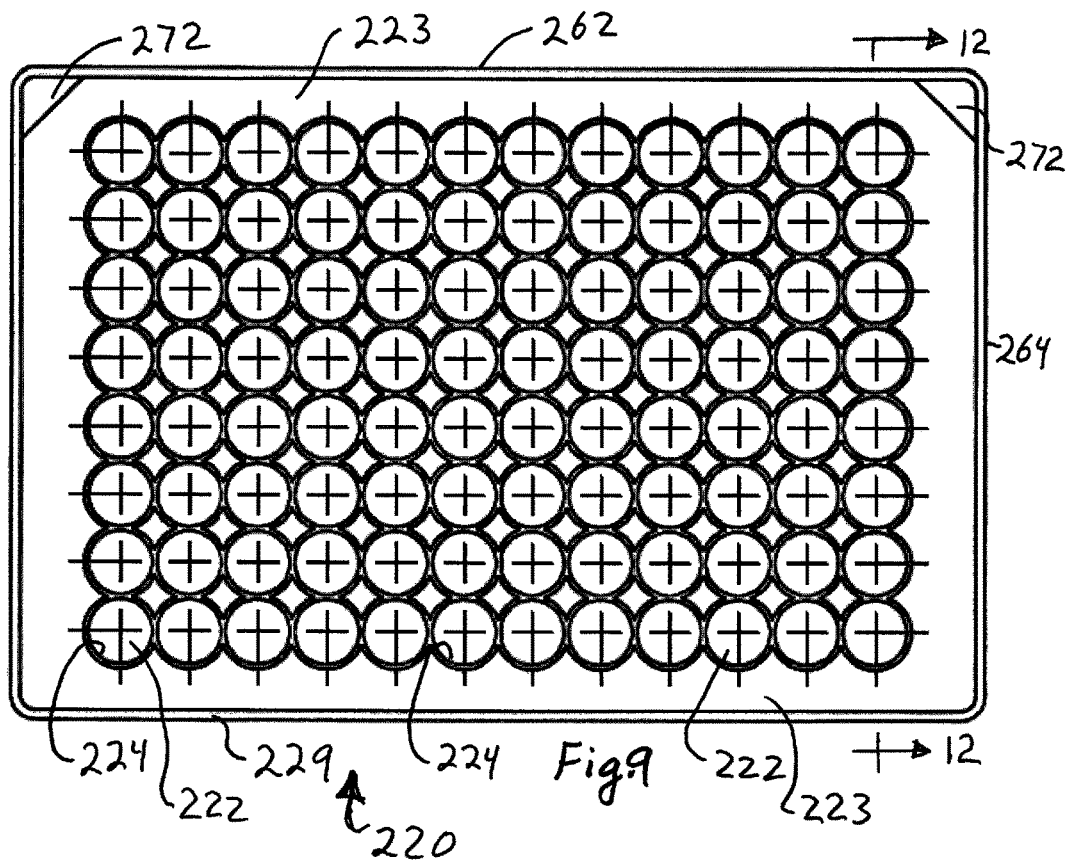
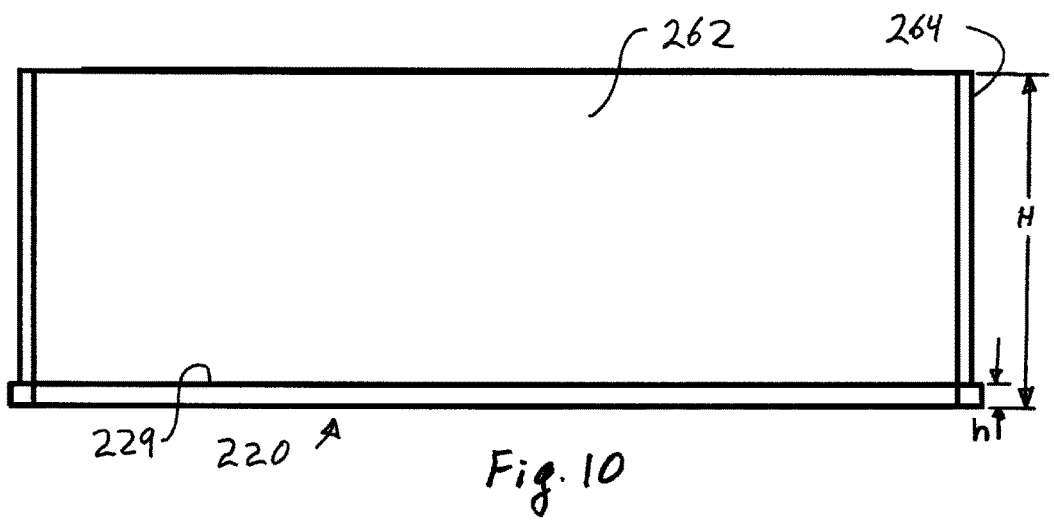

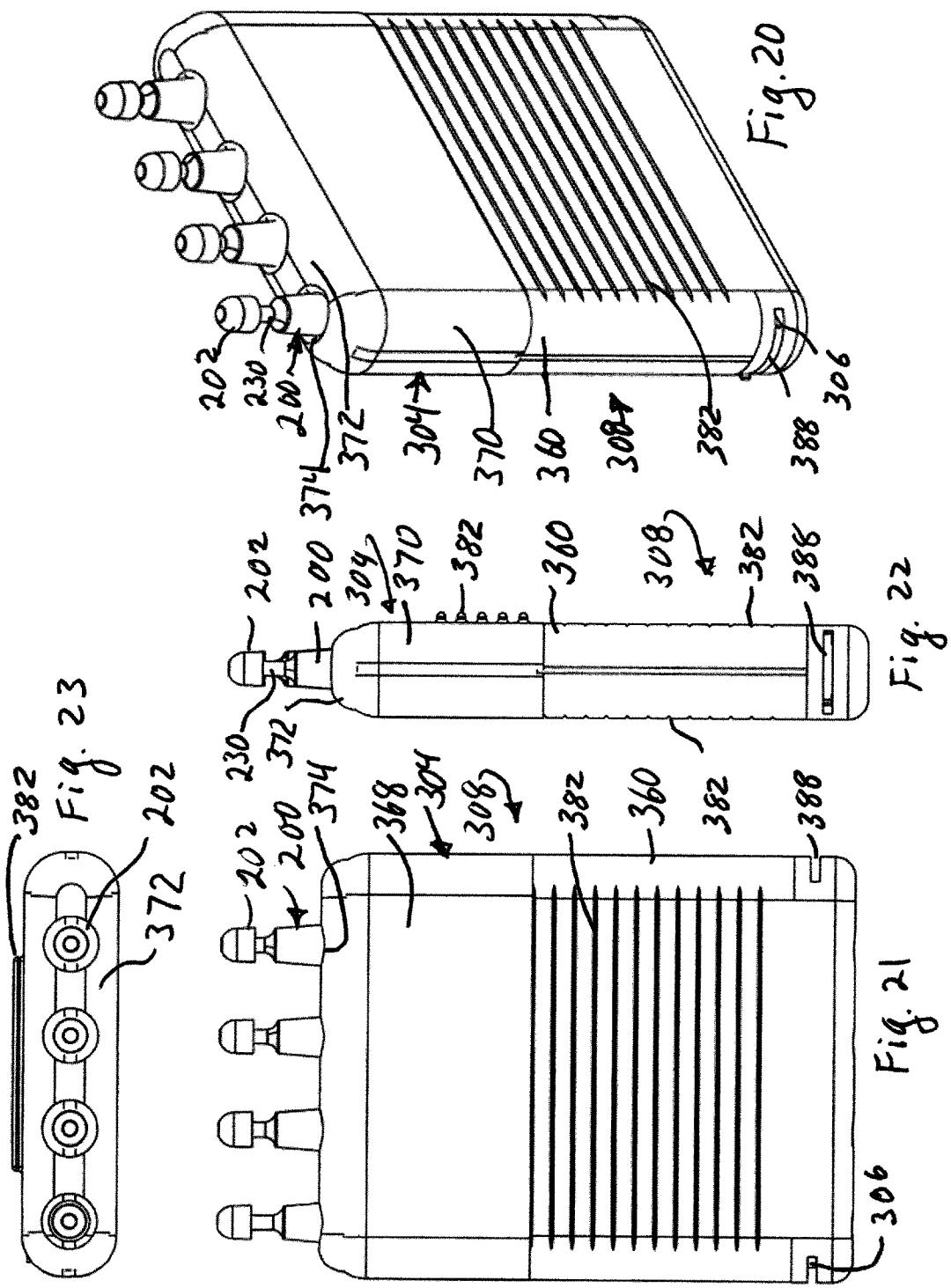

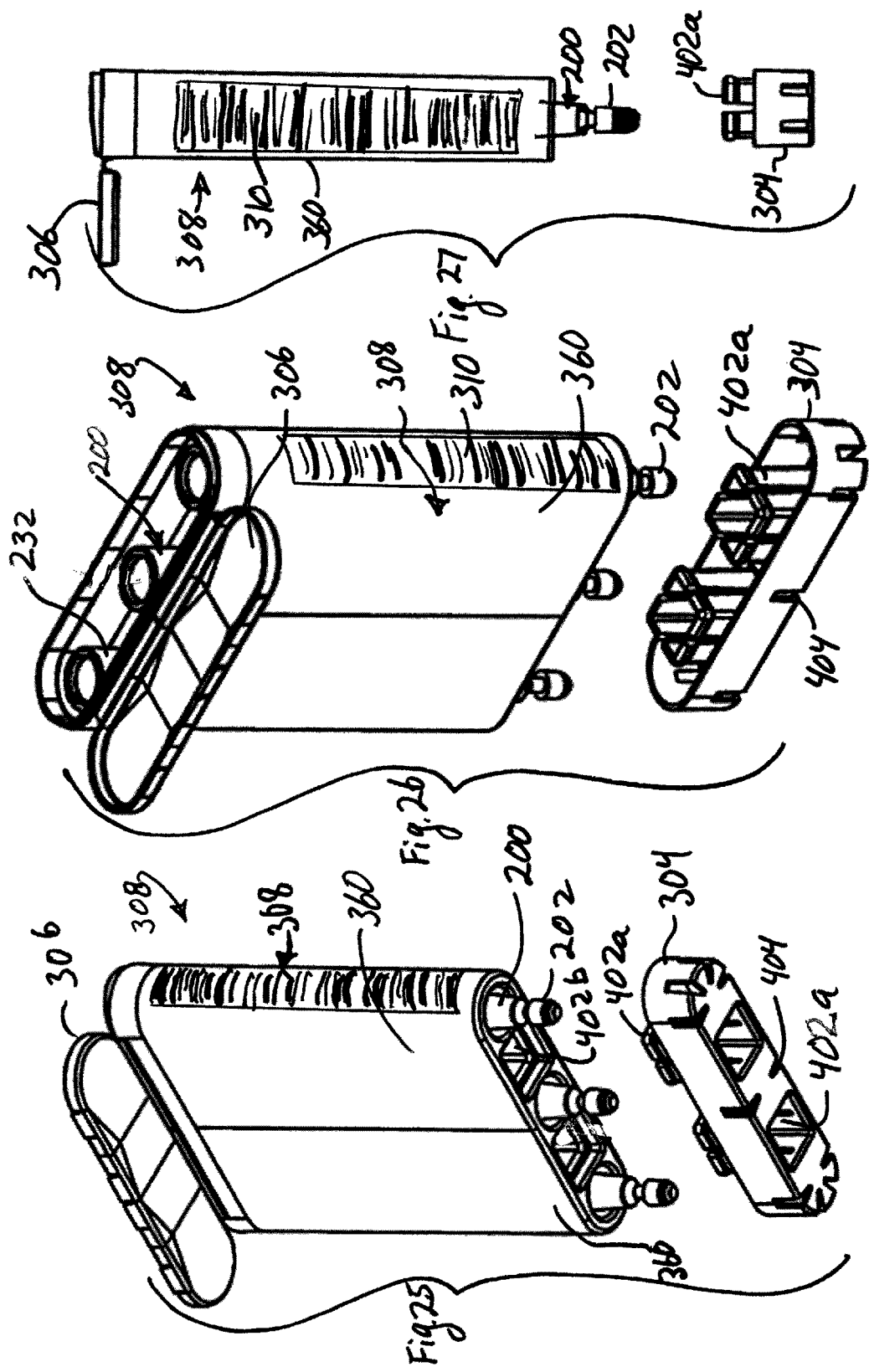

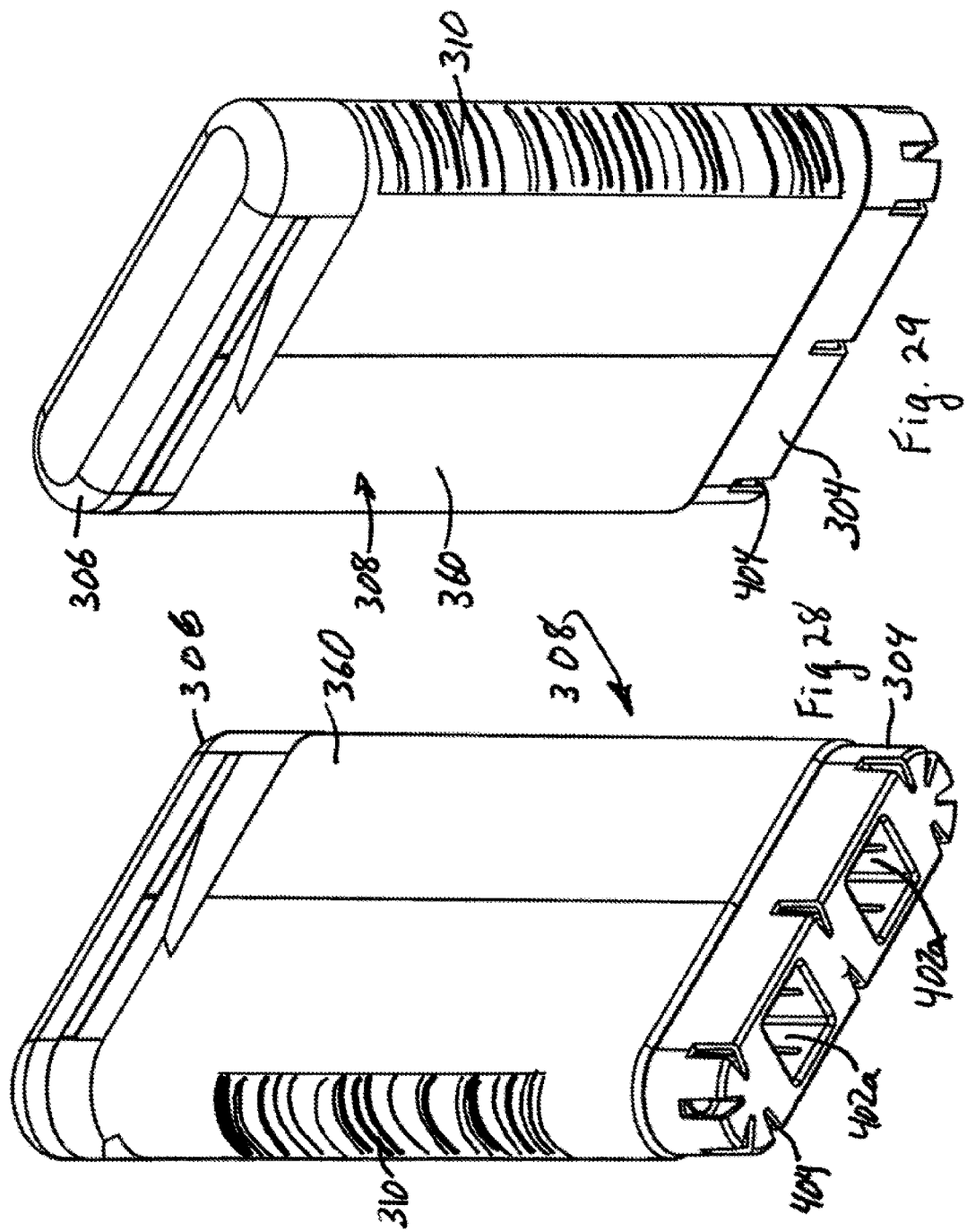

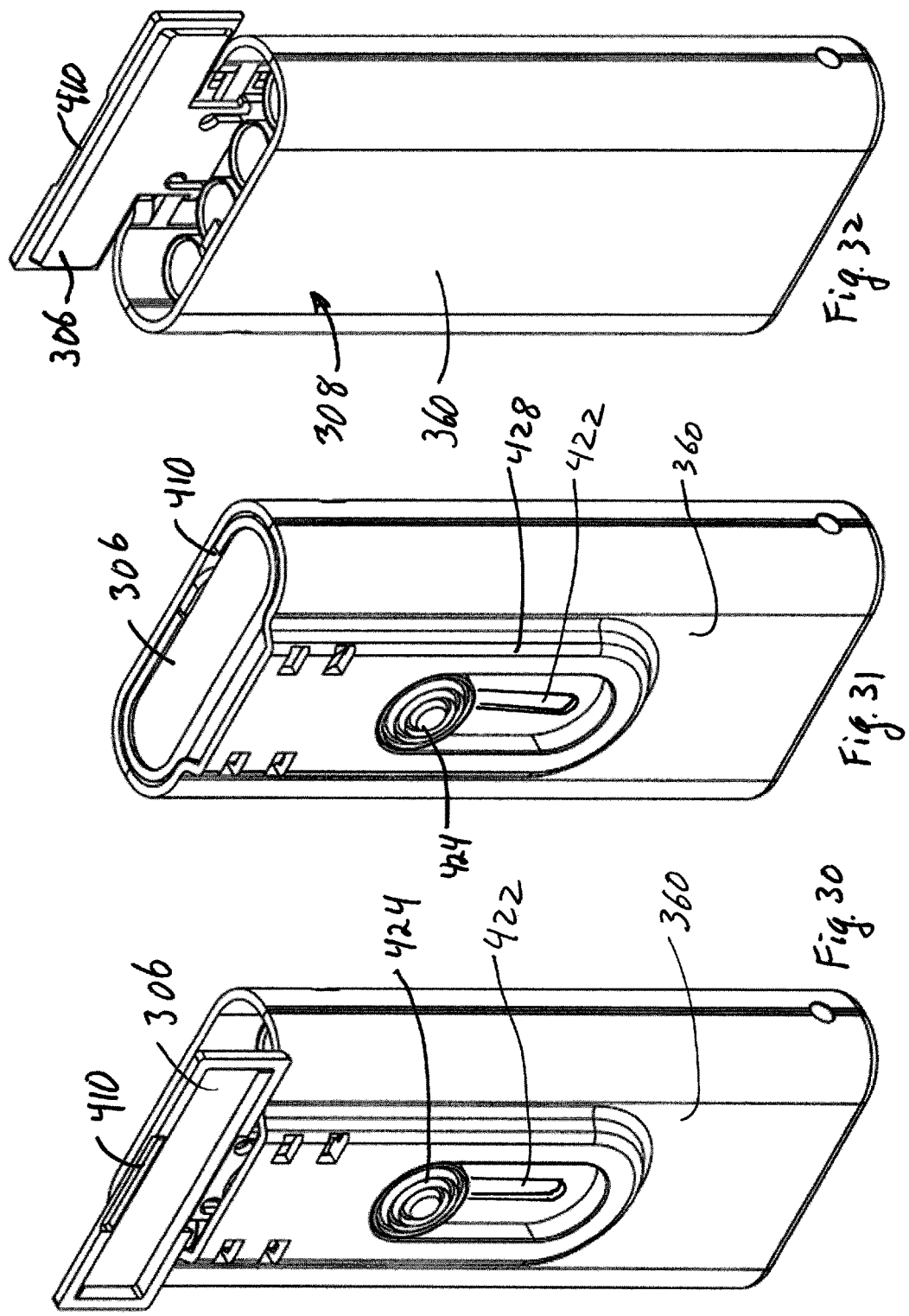

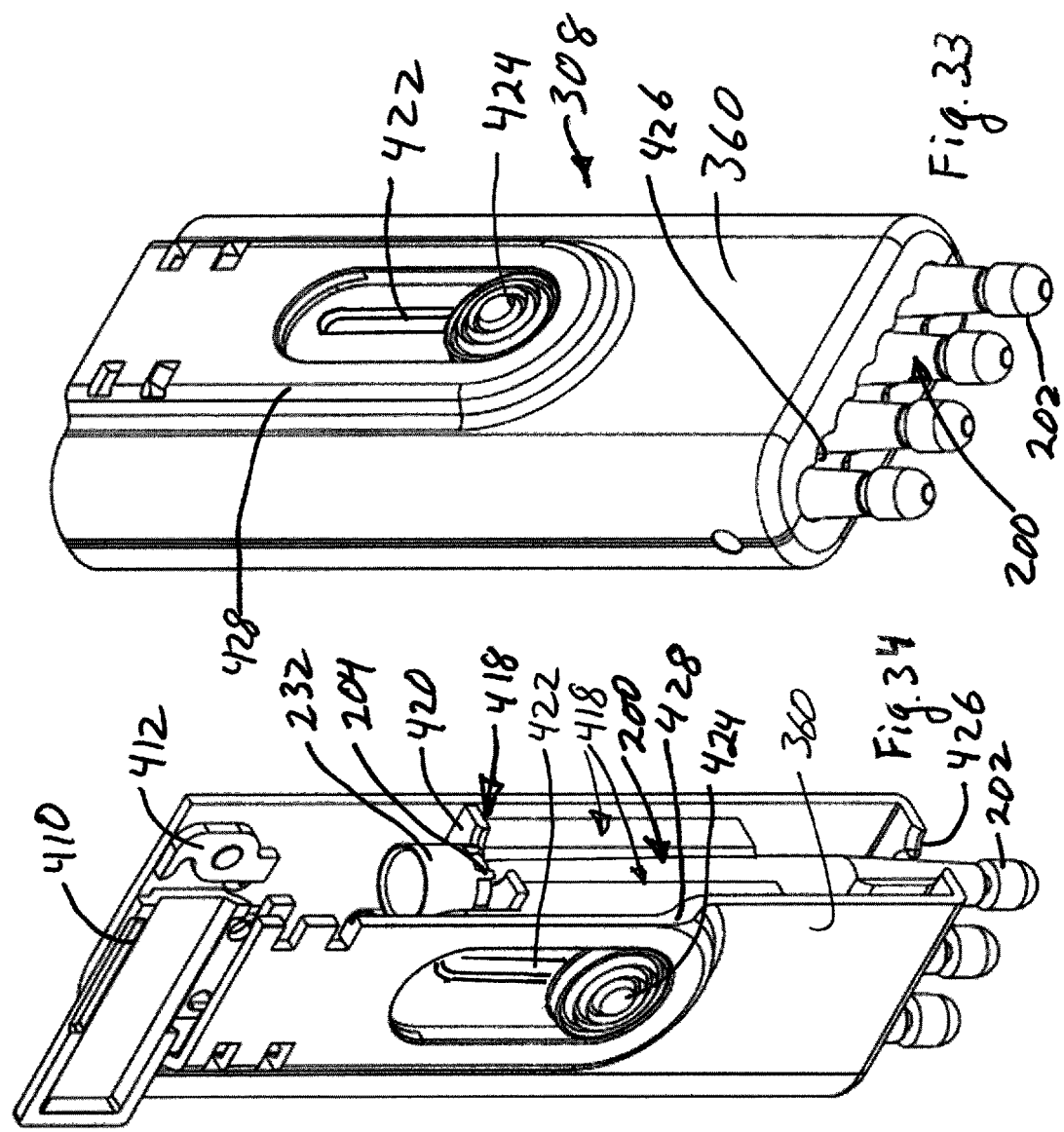

METHOD AND APPARATUS FOR HANDLING BLOOD FOR TESTING

CROSS-REFERENCE TO RELATED APPLICATIONS

The application claims the benefit under 35 U.S.C. § 119(e) to Provisional Patent Application No. 62/149,415 filed Apr. 17, 2015, the entire contents of which are incorporated herein by reference.

BACKGROUND OF THE INVENTION

This application relates to a method apparatus for sampling bodily fluids such as blood, for use in testing, research or for diagnostic use.

Multiple blood samples are used for clinical trials for pharmacokinetic analyses. Other fluid samples are needed for drug testing, crime scene investigations and patient analysis for various medical conditions. Field samples of various contaminated substances or unknown substances are collected for later laboratory analysis in a variety of applications.

Absorbent tips and holders for those absorbent tips have been developed by various companies, including those disclosed in application Ser. No. 13/668,062 filed Nov. 2, 2012. But a need for improved, absorbent tips on holders configured for ease of handling and for efficient handling still remains. There is thus a need for an improved method and apparatus for use in fluid sampling. There is a further need for efficient handling of the absorbed fluid samples.

SUMMARY

A holder rack has an array of tubular slots. Plural holders each having an absorbent tip are held in the slots. The rack maintains the absorbent tips in position and prevents lateral movement to avoid contamination of dried fluid samples contained in the absorbent tips. The holder rack fits over and mates with a common microtiter well plates to accurately position one absorbent tip adjacent a bottom of a well in each well of the well plate. The holder rack has side openings allowing the rack and mated well plate to be placed on processing equipment and processed as a single unit, while maintaining the position of the absorbent tips in the wells so the dried samples can be extracted from the tips. Following extraction, the rack and tips are removed from the well plate, with the extracted samples in the well plates undergoing further processing or analysis. The holders are removed from the holder rack and discarded using appropriate safety procedures commensurate with the nature of the samples and holders.

The holders advantageously have first printed indicia thereon containing information relating to the sample such as a patient's name, date of acquisition, testing facility and other relevant information. The holders have an absorbent tip that quickly absorbs a predetermined volume of fluid, with the user placing the holder in a container for drying. After the sample is dried, the absorbent tip is covered by a cap and as need the holder is enclosed by a lid to form a sealed shipping container which is sent to a processing facility. The testing container is provided with second printed indicia which contains some, all or more of the information in the first printed indicia. The user may scan or otherwise record the information in the first and second printed indicia and preferably transmits some or all of that information to the processing facility.

The processing facility scans or otherwise acquires the information from the second printed indicia on the container, removes the holders from the container an scans or otherwise acquires the information from the first printed indicia on each holder and compares the information in the first and second printed indicia to verify the appropriate holders are received for processing. Each holder is placed in a different slot or opening in the holding rack and the identification of the rack and the slot within which each holder is placed are tracked. Advantageously once the containers are placed in the holding tray, the opening of the containers, the scanning of printed indicia on the containers, the removal of the holders from the container, the scanning of the printed indicia on the holders, the placement of the holders in the holding rack, the placement of the holding rack on the well plate, the extraction of the sample from the absorbent tips of each holder, the removal of the holder and holder rack from the well plate, the removal of the holder from the holder rack may all be performed by automated mechanisms with no need for manual movement of the holders, racks or well plates. The extracted samples are then moved on to analysis, or directly analyzed in some cases, by a variety of means such as LC/MS/MS, immunoassay, or combinations thereof. The results of the analysis of the extracted samples are provided to the user acquiring the sample, or the employer of the user, or directly to the source of the sample if they are a person or patient, or to other locations as directed (e.g., a doctor for evaluation).

There is thus advantageously provided an assembly for use with analyzing a sample contained in an absorbent tip on a distal end of an elongated holder where the holder has a length L between a distal end of the absorbent tip and a distal end of a projection extending outward from a proximal end of the holder. The sample to be extracted uses a well plate having a height H and an outwardly extending ledge around at least a portion of the bottom of the well plate with the ledge having a height h. The wells are arranged in a square grid work with each well having a closed bottom and a longitudinal axis parallel to the axis of the other wells. The assembly includes a rectangular holding rack having four corners. The rack has top with a plurality of slots extending through the top and opening onto a top surface of the top. The slot openings are arranged in a square grid work corresponding to that of the well plate's grid work. Each of the plurality of slots has a longitudinal parallel to the axes of the well plates during use and sized to engage and hold a holder during use. The rack also has a plurality of the slots each extending through the top and configured relative to the holders to position the holders that are inserted into the slots during use of the rack at a predetermined location within each slot. The rack further has a leg extending downward at each corner a predetermined distance h. Each leg has two side portions each extending toward a different adjacent corner so the two side portions at each corner are substantially perpendicular to each other. Each side portion ends a distance spaced apart from the side portion extending from the adjacent corner with the distance being slightly less than D measured at the bottom of the well plate during use. The rack also has a tab on at least one side portion of each leg with the tab extending beyond a bottom of the at least one side portion a distance less than h. The tab is also offset from a plane of the at least one side portion on an outer surface of that at least one side portion. The legs are configured to nest over the well plate with the lower surface of the side portions abutting the ledge of the well plate.

In further variations, the rack also has at least one holder inserted into at least one of the slots with the bottom end of the projection on the holder being spaced a distance of L from a distal end of the absorbent tip, and with the distance L being selected to place the absorbent tip adjacent a bottom end of the well into which the at least one holder is inserted when mated with a well plate so the bottom of the side portions abut the ledge of the well plate. Advantageously, there are at least three projections on the holder to help define the alignment of the holder. Further, the length L is advantageously within about 90% of the distance from the top of the one of the slot openings to the bottom of one of the side portions measured along the longitudinal axis of the at least one holder when inserted into the one of the slot openings so the projection of the at least one holder abuts the top of that slot opening. Additionally, the assembly may have the absorbent tip of one of the holders, containing a dried sample. The rack may have a gripping surface on two opposing sides of the rack configured to engage a gripper of an automated device.

The assembly may also include the well plate having a height H and an outwardly extending ledge around at least a portion of the bottom of the well plate with the ledge having a height h. The well plate may have a plurality of wells arranged in a square grid work with each well having a closed bottom and a longitudinal axis parallel to the axis of the other wells. The length L is advantageously selected to position the distal end of the absorbent tip of the at least one holder adjacent the closed end of the well into which the at least one holder is inserted when the rack is mated with the well plate. Advantageously, the plurality of wells each contains a fluid selected for processing a sample. Moreover, the distance D is advantageously selected to allow a gripping device to engage the ledge and hold the well plate and rack to a processing apparatus and wherein a plurality of the slots have a larger diameter at the top of the slot and a smaller diameter at a bottom of the slot. Additionally, the holder may have first printed indicia thereon containing information relating to the holder and a sample absorbed in the absorbent tip.

There is also advantageously provided a kit for collecting and analyzing fluids. The kit may include a plurality of holders each having a proximal end with an outwardly extending projection thereon and a distal end having an absorbent tip thereon, with a distance L between the projection and the distal end of the tip. The kit may further include a container having a plurality of compartments, with each compartment configured to releasably receive a different one of the holders and maintain the absorbent tip of the different one of the holders from contacting the compartment or another absorbent tip. The container preferably has a cap configured to enclose the absorbent tips during shipment of the container. There is preferably first printed indicia on each holder with the indicia containing information relating to the holder. Second printed indicia on each container may contain information relating to the container and the holders within the container.

The kit preferably includes at least one holder rack having four corners. The rack may include a top with a plurality of slots extending through the top and opening onto a top surface of the top. The slot openings are arranged in a square grid work corresponding to that of the well plate's grid work. Each of the plurality of slots has a longitudinal parallel to the axes of the well plates during use and sized to engage and hold a holder during use. A plurality of the slots each extend through the top with the slots sized to position holders inserted into the slots at a predetermine location during use of the rack. Advantageously, each slot has a larger diameter at the top of the slot and a smaller diameter at a bottom of the slot to help position the holders. The rack also has a leg extending downward at each corner a predetermined distance h, with each leg having two side portions each extending toward a different adjacent corner so the two side portions at each corner are substantially perpendicular to each other. Each side portion ends at a distance spaced apart from the side portion extending from the adjacent corner with the distance being slightly less than D when measured at the bottom of the well plate during use.

The kit also has a tab on at least one side portion of each leg. The tab extends beyond a bottom of the at least one side portion a distance less than h. The tab is also offset from a plane of the at least one side portion on an outer surface of that at least one side portion. The legs are configured to nest over the well plate with the lower surface of the side portions abutting the ledge of the well plate. The legs and/or the tabs restrain lateral movement of the holding rack relative to the well plate when the side plates abut the ledge of the well plate.

In further variations, the kit also has at least one holder configured to be inserted into at least one of the slots with the bottom end of the projection being spaced a distance of L from a distal end of the absorbent tip, and with the distance L being selected to place the absorbent tip adjacent a bottom end of the well into which the at least one holder is inserted when mated with a well plate so the bottom of the side portions abut the ledge of the well plate. The distance D is advantageously selected to allow a gripping device to engage the ledge and hold a well plate mated to the rack in operating contact with a processing apparatus. The rack advantageously has a gripping surface on two opposing sides of the rack with the gripping surface configured to engage a gripper of an automated device. The well plate advantageously has a height H and an outwardly extending ledge around at least a portion of the bottom of the well plate with the ledge having a height h. The well plate also preferably has a plurality of wells arranged in a square grid work with each well having a closed bottom and a longitudinal axis parallel to the axis of the other wells, with the length L being selected to position the distal end of the absorbent tip of the at least one holder adjacent the closed end of the well into which the at least one holder is inserted when the rack is mated with the well plate.

BRIEF DESCRIPTION OF THE DRAWINGS

These and other advantages and features of the invention will be better appreciated in view of the following drawings and descriptions in which like numbers refer to like parts throughout, and in which:

FIG. 1 is a an exploded view of a holder for micro-titer well plate onto which a rack nests and a holder and its absorbent tip that may be held in the rack with the tip in the well plate;

FIG. 2a is a front view of the holder of FIG. 1 without an absorbent tip, with the back view being a mirror image thereof;

FIG. 2b is a bottom view of the holder of FIG. 2a;

FIG. 2c is a sectional view of the holder of FIG. 2a;

FIG. 3a is a phantom perspective view of an absorbent tip for use with the holder of FIG. 2a;

FIG. 3b is a bottom plan view of the absorbent tip of FIG. 3a;

FIG. 3c is a front view of the absorbent tip of FIG. 3a, with the opposing back view being a mirror image thereof;

FIG. 4a is a lower perspective view of the holding rack of FIG. 1;

FIG. 4b is an upper perspective view of the holding rack of FIG. 4a;

FIG. 7 is a sectional view taken along section 7-7 of FIG. 5;

FIG. 8 is a sectional view taken along section 8-8 of FIG. 6;

FIG. 9 is a top plan view of the well plate of the well plate of FIG. 1;

FIG. 10 is a front plan view of the well plate of FIG. 9, with the back view being a mirror image thereof;

FIGS. 18a-18e show variations on the configuration of the distal end of a holder for use with an absorbent tips;

FIG. 20 is an upper perspective view of the container of FIG. 14 with the holders in the container and the cap off;

FIG. 21 is a front plan view of the cartridge and holders of FIG. 20;

FIG. 22 is a right side view of the cartridge and holders of FIG. 21;

FIG. 23 is a top plan view of the cartridge and holders of FIG. 21;

FIG. 25 is a lower, exploded perspective of a further embodiment of a cartridge and three holders, with the container lid open;

FIG. 26 is an upper, exploded perspective view of the cartridge and holders of FIG. 25;

FIG. 27 is a side view of the cartridge and holders of FIG. 25;

FIG. 28 is a lower perspective view of the holder of FIG. 25 with the cap on;

FIG. 29 is an upper perspective view of the holder of FIG. 28;

FIG. 30 is an upper perspective view of a further embodiment of a cartridge with a lid that is open and holders in a retracted position;

FIG. 31 is an upper perspective view of a further embodiment of a cartridge with a lid that is closed and holders in a retracted position;

FIG. 32 is an upper perspective view of the cartridge of FIG. 30 taken from the opposing side;

FIG. 33 is a lower perspective view of the cartridge of FIGS. 30-32 with the lid closed and holders moved to an extended position; and FIG. 34 is a partial sectional view of the cartridge and holders of FIG. 34 with a lid open.

DETAILED DESCRIPTION

Figure 5:
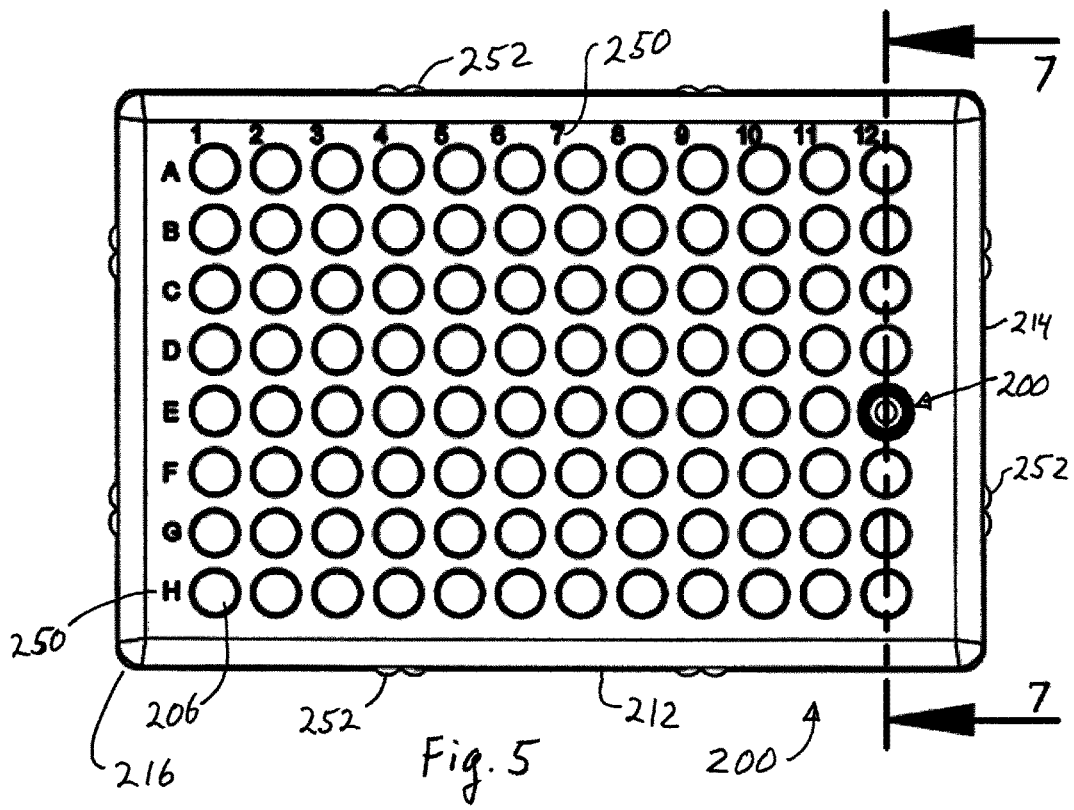
FIG. 5 is a top plan view of the holding rack of FIG. 1 with a holder inserted therein with the holder rack placed over the well plate of FIG. 1.
Figure 6:
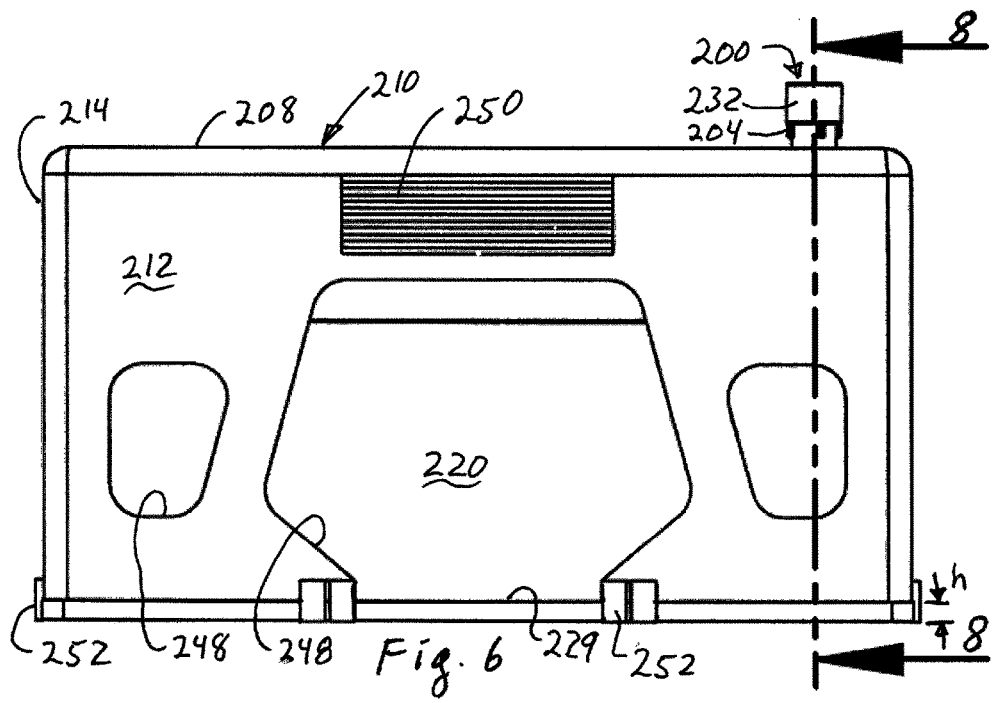
FIG. 6 is a front view of the assembly of FIG. 5 with the holding rack of FIG. 1 mated with the well plate of FIG. 1, with the opposing back view being a mirror image thereof.
Figure 11:
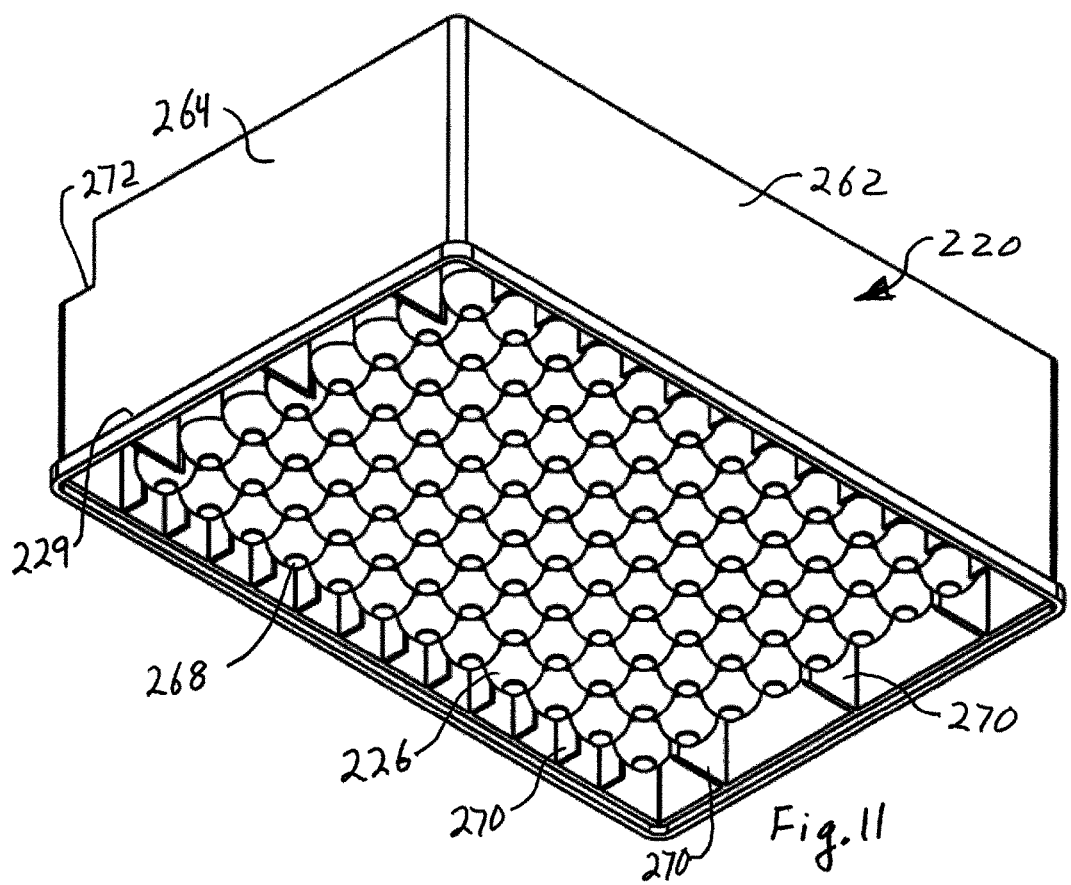
FIG. 11 is a bottom perspective view of the well plate of FIGS. 1 and 9.
Figure 12:
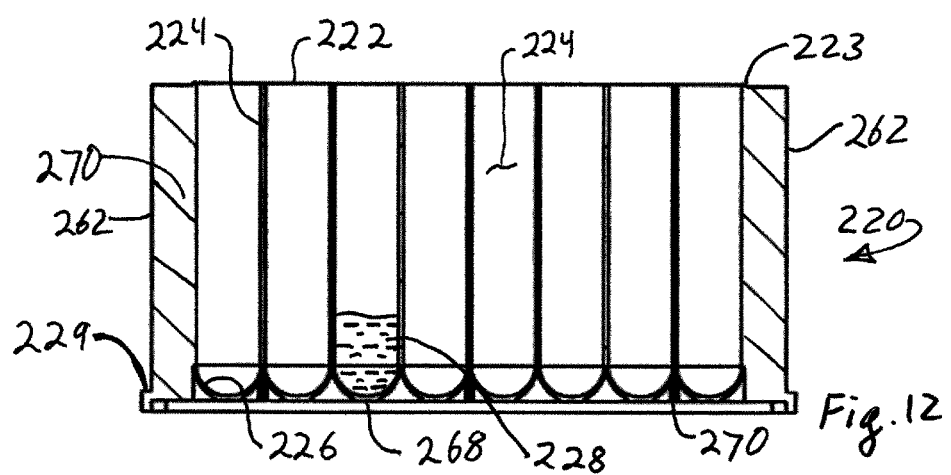
FIG. 12 is a sectional view of the well plate taken along section 12-12 of FIG. 9.

Referring to FIGS. 1-3, a holder 200 has an absorbent tip 202 on a distal end of the holder with a retaining flange or ribs 204 extending outward from the holder at an opposing, proximal end of the holder. Advantageously there are three ribs 204 extending outward in a plane orthogonal to a longitudinal axis of an elongated, tubular holder, with the ribs 204 acting as position stops to orientate the longitudinal axis relative to a surface contacting those stops, and to position the holder relative to those stops and that surface. The holder 200 is configured to be retained in any of openings 206 to generally cylindrical slots that are located in and passing through a top plate 208 in a holding rack 210. The holding rack 210 is configured to support the holders 200 so the absorbent tips 202 are positioned at predetermined locations and to prevent contact of the tips with each other or a support surface during drying. The holding rack 210 when rectangular in shape has opposing front and back sides 212 and opposing ends 214 advantageously forming legs 216 at corners of a quadrilateral-shaped drying rack 210. The legs 216 and/or sides and ends 212, 214 are advantageously configured to mate with a well plate 220 having a plurality of wells or recesses 222. The legs 216 cooperate with the corners and sides of the well plate 220 to help restrain lateral movement of the rack and well plate. Each well 222 has an opening 224 on an upper plate opposite an end 226 (FIG. 7) of the well which end is typically closed during extraction. The end may be opened to drain fluid or filter fluid but during extraction the end is typically closed. Thus, as used herein a closed end in the well plate does not require the end be permanently closed.

The well plates are designed to a standard, ANSI/SLAS 1 to 4-2004, and 1-2006. The standards define the well plate external dimensions, flange dimensions, height, well shape and other dimensions. The openings 224 are in top plate 223 of the well plate 220. The rack is configured to mate with these well plates using the advantageous features described herein.

A plurality of the wells or recess 222 advantageously, but optionally have an opening 224 located to configured and located to receive a holder 200 placed in the openings 206 of the holding rack 210. The wells 222 advantageously have a closed end 226 to retain a fluid 228 (FIG. 7), such as an extraction fluid suitable for extraction of the bodily fluid retained in the absorbent tip 202 of the holder 200 associated with the tip. An outwardly extending flange 229 or rib on the well plate 220 advantageously cooperates with the sides 212, ends 214 or legs 216 of the holding rack 210 to position the holding rack relative to the well plate and thus position the holders 200 and holder tips 202 relative to the extraction fluid 228 when the holding rack is mated with the well plate. The outward extending flange 229 has a height h, and the well plate has an overall height H, measured along axis 238.

As used herein, the relative directions and terms upper, lower, above and below refer to relative directions or positions along the longitudinal axis 238 (FIG. 1) of the holder 200 when in the holding rack 210 and well plate 220. When those parts rest on a working surface the axis 238 is generally vertical. The distal end of the holder corresponds to the bottom end of the holder. The proximal end of the holder corresponds to the upper end of the holder. The lateral direction is orthogonal to axis 238.

Referring to FIGS. 1-3 and 7, the holder 200 is preferably tubular and has a closed distal end configured to mate with and hold the absorbent tip 202. In the depicted embodiment the distal end of the holder 200 has a projecting tip 230. The end of tip 230 is preferably, but optionally rounded to help avoid damage to the absorbent tip 202 which is fastened to the tip 230. The body of the holder 200 advantageously is generally cylindrical with a slightly conical taper adjacent the distal end terminating in a closed end that forms the tip 230. The proximal end of the holder 200 opposite the tip 230 has an enlarged head 232 forming a flange or ledge 234 facing toward the tip 230. A head 232 with an offsetting flange or ledge 234 extending radially a few millimeters is believed suitable for use. At least one and preferably a plurality of ribs extend outward from the body of the holder 200 adjacent to and preferably from the bottom of the head 232. The ribs 204 terminate in a plane orthogonal to the longitudinal axis 238 of the holder 200, preferably at a predetermined distance from the proximal end of the holder 200 and at a predetermined distance from the distal end of the tip 230 and the distal end of the absorbent tip 202. Thus, a lower end of the ribs 204 are a known distance from the other parts of the holder 200, especially the tip 230 and absorbent tip 202. Advantageously, the lower surface of the flange or ledge 234 is also located a predetermined distance from the distal end of the tip 230 and from the distal end of the absorbent tip 202 and from other parts of the holder 200.

The absorbent tip 202 can have various shapes as shown in FIGS. 3, 18a-18d, and 19a-19b. The tip 202 shown I FIGS. 3a-3c has a flat lower end 240 with a circular periphery joining outwardly or convexly curved sides 242 that join a generally cylindrical upper portion 244. The flat lower end 240 may be a slightly offset cylinder having a short sidewall of about 1-3 mm with the curved sides 244 joining the base of that short cylinder. A recess 246 is formed in the upper end of the absorbent tip. The recess 246 and tip 230 are configured to mate with each other and preferably have generally cylindrical shapes. In use, the absorbent tip 202 is press fit onto the holder's tip 230. The tip is made of various absorbent materials discussed later. As needed, the tip 230 may have ridges or barbs (not shown) on its outer surface to resist easy removal of the absorbent tip 202 from the tip 230. Adhesives, ultrasonic bonding or other attachment mechanisms may be used to connect the absorbent tip 202 to the holder tip 230, but are not preferred.

Referring to FIGS. 1, 4-6 and 7, the holding rack 210 is shown with a quadrilateral shape. A plurality of through-holes or slots with openings 206 are arranged in an array to correspond with the wells 222 in well plate 220. The depicted holding rack 210 has 96 openings 206 arranged in a rectangular grid. This corresponds to a 96 well well-plate. Printed indicia 250 along at least one side or end of the holding rack can be used to identify each opening as is known in the art. In the depicted holding rack numbers 1-12 extend along one side with letters A-H extending along an adjacent end. The printed indicia 250 is advantageously molded into the rack 210, which is preferably made of a plastic or polymer suited for use with the samples and processing chemicals so as not to react with the samples or chemicals or analytical equipment. The depicted holder 200 of FIG. 1 is aligned with opening 202 having position or identification number E12. The top plate 208 is preferably flat so that it may be positioned parallel to but offset a predetermined distance from the flat top surface 223 of the well plate 220. The holding rack 210 is generally box shaped but the sides and ends may have various openings 248 formed therein in order to reduce the weight and to allow air circulation during drying of the absorbent tips 202 when holders 200 are held in the holding rack and the rack rests upon a support surface. The openings 248 preferably extend to the bottom edge of the sides 212 and ends 214 so as to form legs 216 each having a portion of an adjacent side 212 and an adjacent end 214 forming each leg. Advantageously, an opening 248 extends along a bottom edge of each side 212 and end 214 at the middle of the respective side and edge and such openings are large enough to allow attachment mechanisms from shakers or heaters or manipulating equipment to releasably the ledge 229 or sides adjacent the ledge at the middle of the sides and ends of the well plate. The distance between the side portions 212, 214 of each leg 216 at the location of the openings 248 at the bottom of the side portions, is preferably a distance greater than or slightly greater than D, where D is the distance needed to accommodate gripping surfaces on various processing equipment (e.g., shakers, heaters) to hold the well plate 220 to the equipment during processing.

One or more gripping surfaces 236 are placed on the sides of the rack 210. The gripping surfaces are preferably a series of parallel ridges separated by grooves all parallel to an edge of the top plate 208. The gripping surfaces 236 are preferably located at the center of two opposing sides or ends of the rack 210. The gripping surfaces are advantageously configured to releasably engage with robotic grippers to make it easier to securely grab and move the rack 210 with one or more holders 200 in the rack.

At the bottom of each side 212 and end 214 is preferably located a tab 254 so there are preferably four tabs 254. Advantageously, there are at least four tabs 254 and preferably there are eight tabs. If four tabs are used they are advantageously used at the four corners joining sides 212 and ends 216. If eight tabs 254 are used they are advantageously located at the bottom edge of the sides and ends adjacent the openings 248 in the sides and ends. The tabs advantageously extend beyond the bottom edge of the sides 212 and ends 214 to provide a stand-off-tab that prevents the tips 202 from abutting a work surface upon which the rack 210 rests during use as the rack rests on the bottom ends of the tabs rather than the edges. The tabs 254 preferably extend along the outside or exterior surface of the sides 212 and 214 so the tabs are offset from but parallel to the planes containing the respective sides 212 and ends 214. That offset allows the tabs to fit along the outer side of the flange 229 (FIG. 1) on the bottom of the well plate 220 and helps align the holding rack 210 with the well plate 220 when those parts are mated together. Further, because the tabs 254 extend along the outside of the edges 229 the tabs help restrain lateral movement of the rack 210 relative to the well plate 220 when those parts are mated together. Moreover, the tabs 254 are long enough that when the holders are in the slots the distal end of the absorbent top 202 does not abut the surface on which the rack rests. The tabs 254 thus advantageously help offset the bottom edge of the holding rack 210 from the supporting surface on which the rack can rest during drying of the absorbent tips 202 in the holders 200 placed in the rack (to avoid contamination from that surface), and the tabs may optionally further help position the drying rack on the well plate 220.

Referring to FIGS. 1 and 4-8, the openings 206 in the top plate 208 of holding rack 210 extend through the thickness of the holding rack's top. The top plate 208 is preferably fairly thick or deep along the length of axis 238 (FIG. 1) so that each of the openings 208 forms one end of a generally cylindrical slots or passages 256 defined by walls that advantageously taper slightly toward the bottom of the plate to form a slightly conical passage 256 as best seen in FIG. 7. A passage 256 having a length parallel to axis 238 of about and a smaller diameter slightly greater than about 0.3 inches (about 8 mm) is believed suitable for use with a holder 200 having a diameter of about 0.3 inches and a length of about 2.8 inches (about 70 mm). Each passage 256 is preferably slightly larger at the top opening 206 and slightly smaller at the lower end of the passage 256 to make it easier to insert the holder 200 into the passage 256, and to help achieve a close fit between the walls forming passage 256 and the side walls forming holder 200.

As seen in FIG. 4a, the bottom or interior side of the top plate 208 may have a plurality of smaller blind holes 258 in the middle of each group of four passages 256 that are arranged in a square. The top plate 208 may be molded and the blind holes 258 help provide a more uniform wall thickness to the passages 256 to improve accuracy of the shape of the passages 256. The holes 258 may thus vary or be omitted depending on manufacturing considerations. The interior thickness of the top plate 208 may extend to the side walls 212 and end walls 214, but preferably the interior of the top plate is spaced apart from the interior of the walls 212 and 214 and intermittently connected to those walls by stiffening struts 260. The number, configuration and location of the stiffening struts 260 will vary. Thus, in the depicted embodiment the top surface of top plate 208 extends to the side walls 212 and end walls while the interior of the top plate 208 is separated from those side walls along a substantial length of the interior of that top plate, but with periodic connections by stiffening plates 260. This configuration is believed to provide a light weight but sturdy holder plate that accurately positions the holders 200 in the openings 206 and passages 256. The axes 238 of each passageway 256 are aligned to a sufficiently high degree of accuracy so that the holders 200 and absorbent tips 202 are at predetermined locations in the plane of the top plate 258 with the axes 238 perpendicular to that plane, when the holders are fully seated in the passageways 256.

Referring to FIG. 7, the enlarged head 232 on the proximal end of the holder 200 is preferably configured so it may be engaged by a pipette tip holder or connection on automated equipment. The ribs 204 on the enlarged head 232 have a lower end that abuts the top or exterior surface of the top plate 208. Because the lower end of the ribs 204 are in a plane orthogonal to the axis 238 of each holder 200, the ribs 204 align each holder perpendicular to the top surface of the top plate 208. Because the bottom or lower end of the ribs 204 are a known distance to the distal end of the tip 230 and/or absorbent tip 202, the position of the absorbent tips relative to the top surface of top plate 208 are known. Thus, the position of the absorbent tips 230 of each holder may be accurately positioned to be in substantially the same plane at predetermined locations in a square grid work. The absorbent tips are believed to be positionable within an accuracy of about 1-5 mm and preferably about 0.5-1 mm.

Referring to FIGS. 1, 7 and 10-12, the well plate 220 has two opposing side walls 262 and two opposing end walls 264 joined to top surface 223. A plurality of wells or recesses 222, each with opening 224 in the top surface 223, are preferably arranged in a grid pattern (FIG. 9) in the well plate. The wells 222 are generally cylindrical with bottom-ends 226 that are closed during extraction and preferably, but optionally, domed, forming a half spherical bottom with a diameter about the same as the bottom. Various shaped bottoms are used in current well plates and the bottoms may thus be curved, V-shaped, stepped or flat bottomed. FIG. 7 shows an unlabeled curvature line where the spherically-curved end joins the straight portion of the cylindrical sides of the recess or well 222. The exterior of each bottom end 226 may have a flat, cylindrical portion 268 (FIG. 11) on it for ease of molding and to avoid a curved surface at a location where it may be more easily damaged. Stiffening struts 270 (FIG. 11) may extend between the interior of the walls 262, 264 and the adjacent interior surfaces of the recesses or wells 222. Fluid 228 may be placed in one or more wells 224 (FIGS. 7, 12) and during use will normally be placed in the bottom of each well.

The holder plate has two recessed bosses 272 at opposing corners of one side 220 of the well plate. The bosses 272 are formed by recessing the corners at about a 45 degree angle from the top plate 223 down until the location of the recessed boss 272 about ¼ to ⅓ the height of the well plate. The bosses 272 are on the corners adjacent passages A1 and A12 when the holder plate is on the well plate and serve as alignment and orientation references as is known in the art.

In use, the absorbent tip 202 is placed in contact with a fluid and absorbs that fluid. The tip 202 is advantageously configured to absorb a predetermined volume of fluid in a very short amount of time, typically measured in seconds. The holder 200 is placed in a passageway 256 of the carrier plate without the absorbent tip abutting the sidewall defining that passage 256. When the bottom ends of the ribs 204 abut the top surface of the top plate 208 the holder cannot be inserted further and rests in the holder rack 210. Advantageously the holder 200 is not released until the ribs 204 abut or are very near the top surface of top plate 208. The slight taper on the passage 256 helps center and position the holder 200 in the holding rack 210 and thus positions and holds the absorbent tip 202 and absorbed sample on that tip 202. When the holder rack 210 is resting on a horizontal surface through the tabs 254, the absorbent tip 202 is held in a horizontal X-Y position by the location of the openings 206 and passages 256, and is held in a vertical Z position by the ribs resting on the top surface of top plate 208. The location of a holder within the holding rack 210 may be identified by the printed indicia 250, such as row E and column 12 as shown in FIG. 1. The location and other indicia associated with the sample on absorbent tip 202 may be associated with the holder 200 at various times, preferably before the sample is acquired and placed in the holding rack and more preferably by an electronic or optically readable label.

The holding rack 210 allows air circulation to dry the samples absorbed by the absorbent tips 202. The length of the legs 216 and tabs 252 are selected so that the absorbent tips 202 never extend beyond the plane containing the lower or distal ends of the tabs 252 so the tips 202 do not abut the supporting surface on which the rack 210 rests during drying and thus avoid contamination. The holding rack 210 also keeps the tips 202 laterally apart and further avoids contamination. The length of the passages 256 and the lateral fit between the abutting parts of the 200 and passageway 256 are selected to reduce lateral movement of the absorbent tip 202 to a predetermined amount sufficient to avoid contact with other tips 202 and to provide whatever restriction on movement is desired. Advantageously the holders are positioned and held sufficiently secure that the absorbent tips do not move laterally more than a millimeter or two during use, and preferably move less than one mm laterally during use of the rack and more preferably move less than about 0.5 mm laterally during use of the rack 210. The samples on the absorbent tips may dry by natural air circulation, forced air circulation, heated or unheated, temperature controlled or not, humidity controlled or not, in any desired atmosphere or environment (e.g., air, nitrogen or other inert gas). The entire holding rack 210 and holders are advantageously placed in any desired drying environment to facilitate drying. Alternatively, the holder and absorbent tip may be inserted into the holder rack 210 with the sample already dried.

After the samples are dried to the desired amount, the holder rack 210 and holders 200 may be placed over well plate 220. The four legs 216 of the holding rack 210 fit over the corners of the well plate 220 to help align the two parts as they are mated or nested together. The alignment bosses 272 help orientate the rack and well plate, and using a rectangular shape also helps with the orientation with the holder in the A1 position being in the upper left and the holder in the A12 position being in the upper right. Because the location of the holders 200 are accurately determined the absorbent tips 202 fit into the corresponding openings 224 and associated wells 222 without the absorbent tips 202 abutting the sidewalls of the wells 222. The holder rack 210 may thus be mated vertically with the well plate 220 to place each holder and absorbent tip in a predetermined and correspondingly located well 222, at a predetermined distance from the bottom end 226 along axis 238 of each well 222. Advantageously the lower end of absorbent tip 202 is about 1-2 mm from the bottom end 226 of the well 222. The tabs 254 nest over the ledge 229 on the well plate 220 to restrict lateral movement of the rack 210 and well plate 220.

The length of the legs 216 and side walls 212, 214 are greater than the height of the sides 262, 264 of the well plate 220. But because the absorbent tips 202 are positioned at a known location, when the bottom of the sides 212, 214 abut the ledge 229 on the well plate, the absorbent tips 220 are positioned close to the bottom end 226 of the wells 222 regardless of the height of the well plate. Thus, the length of the tabs the bottom edges of the sides 212, 214 of the rack 210 is selected so that the rack rests on the ledge 229 of the well plate. The absorbent tip is advantageously positioned at a predetermined location in the well 222 because the position of the absorbent tips 202 and various parts of the holder 200 are known relative to the location of the tabs 252 and bottoms of the sides 212, 214 and legs 214 of the holder rack 210.

Advantageously, when the rack 210 and its holders 200 are mated with the well plate 220, the wells 222 have a predetermined fluid 228 in each well, typically an extraction fluid or conditioning fluid selected for use with the analysis of the sample absorbed by the absorbent tip 202. The assembly of the holders 200 held in the holder rack 210 connected to the well plate 220 may be moved as a unit for processing of the absorbent tips 202 within each well 222. The assembly may be placed on heaters or shakers having releasable connectors configured to engage and hold well plates. The openings 248 on the centers of the sides 212 and ends 214 of the holder rack 210 allow the well plate 220 to be connected to such heaters or shakers. The tabs 252 and bottom edges of the legs 213 on the holder rack 210 keep the rack and holders 200 in position relative to the well plate 220 during such processing steps.

Figure 13:
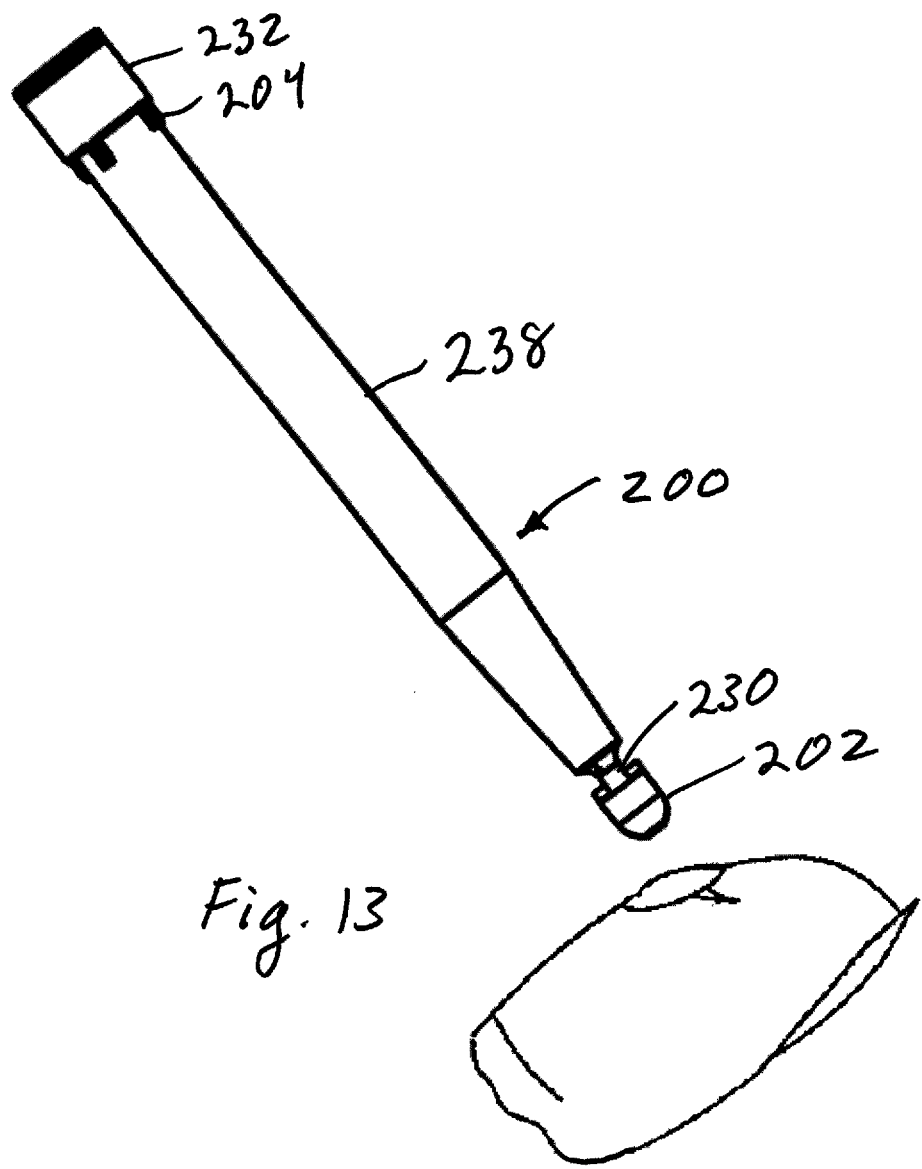
FIG. 13 is a plan view of the holder of FIG. 1 containing printed indicia in the form of a barcode ready to collect a sample.

Referring to FIG. 13, an individual located at home or in the field (hospital, laboratory, pharmacy, doctor's office, outdoor sampling environment) places the absorbent tip 202 into contact with the fluid to be sampled, shown in FIG. 13 as blood from a finger. The absorbent tip 202 absorbs a predetermined sample volume depending on the tip 202. The holder 200 has sample-related printed indicia 300 affixed thereto. The sample-related printed indicia 300 may contain human readable information, machine readable information or both. The sample related information in printed indicia 300 information may relate to the sample absorbed by the tip 200 or the source of the sample, such as patient identification information or patient condition information, including the patient name, date of sample acquisition and personnel acquiring the sample. The printed indicia 300 also preferably contain identification information uniquely associated with the holder 200, such as a serial number in any numerical, alphabetic or alphanumerical format. Machine readable information may include 10-12 digit code 128 Barcode and it may also contain human readable code. Advantageously, the printed indicia 300 are wrapped around the cylindrical portion of the holder 200 so as to be readable in a plurality of radial orientations. A barcode about 1.7 inches long is believed suitable. Typically, various scanners using optical sensors, electronic sensors, magnetic sensors or combinations thereof are used to "read" or otherwise acquire information from the printed indicia 300 at roughly the same time that the sample is collected on the holder 200.

Figure 14:
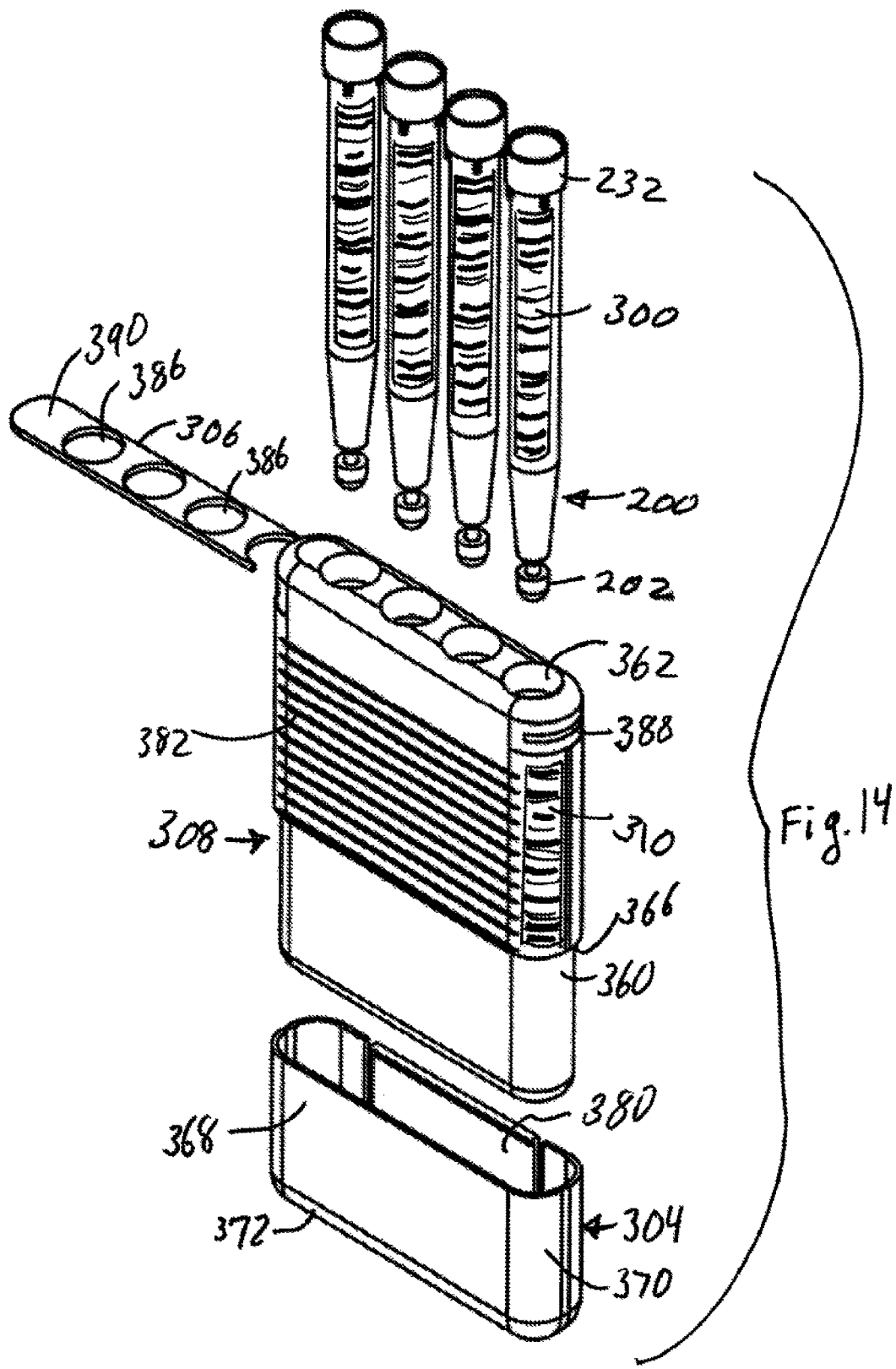
FIG. 14 is an exploded perspective view of a cartridge for containing four depicted holders.

Referring to FIG. 14, the holder 200 is preferably removed from a container or cartridge 308 and after the sample is collected, the holder is reinserted into the cartridge 308. Advantageously, the holder 200 with the sample absorbed onto absorbent tip 202 is placed back into container 308 for drying of the sample. The container 308 is configured to hold the absorbent tip 202 out of contact with other surfaces while the fluid sample dries, after which the absorbent tip 202 is covered with a container cap 304. Optionally, a drying agent may be placed in the container 308 to dry the fluid sample with the drying agent selected to avoid any undesirable contamination of the fluid sample.

The container 308 is shown in FIG. 14 with a sliding lid 306, but advantageously has a hinged lid 306 (FIGS. 25-26) preferably connected to the container by a living hinge, with the lid covering one end of the container. Different hinges can be used but a thin connection between the plastic lid and container is preferred. The container and related parts are preferably made of suitable plastic, advantageously suitable for autoclaving or other sterilization methods. The depicted container 308 has recesses or passages for various numbers of holders 200 with the passages being configured to engage ribs 204 as in the passages 256 of FIG. 7 to help position the holders relative to the container 308, the description of which is not repeated. The lid 306 covers the heads 232 of the holders 200 held in the container 308 to keep them in place during movement of the container. The lid 308 advantageously resiliently contacts the proximal ends of the holders 200 to resiliently urge the ribs 204 against the container 308 to keep the holders from moving during shipment of the container 308.

The container 308 is advantageously but optionally configured to expose the absorbent tips 202 to air for drying. The depicted embodiment of FIGS. 14 and 20-24 achieves this by having a removable cap 304 releasably connect to a distal end of the container 308. Interlocking tabs 302*a* engage recesses (not shown) inside the container 308 to retain the cap 304 on the container 308.

Figure 15:
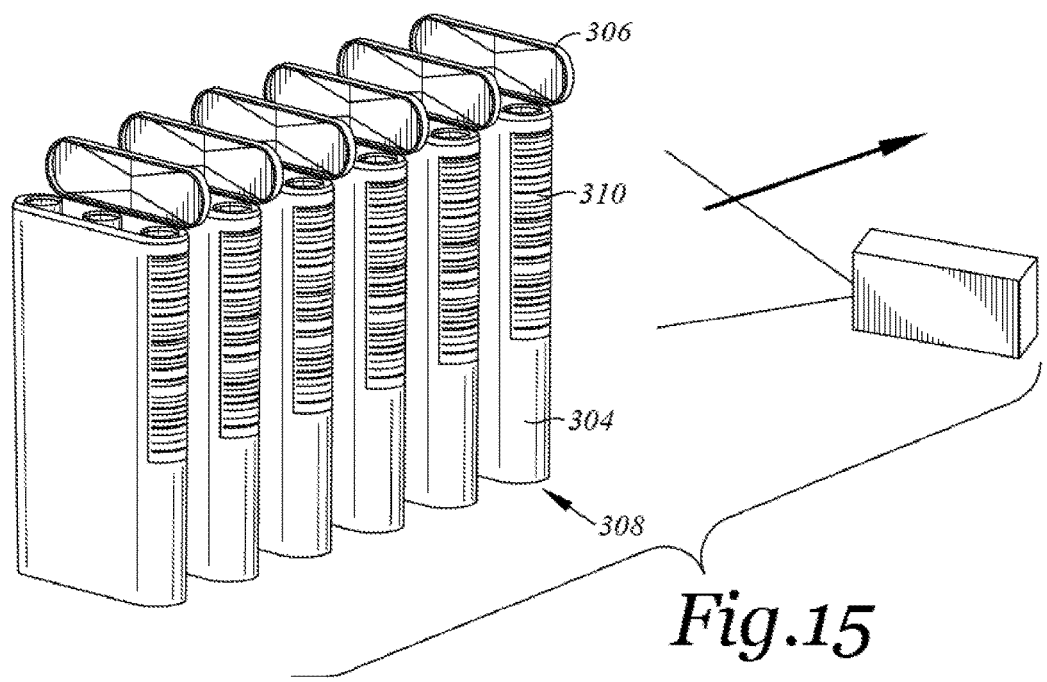
FIG. 15 is a perspective view of a scanner scanning printed indicia on containers.
Figure 16:
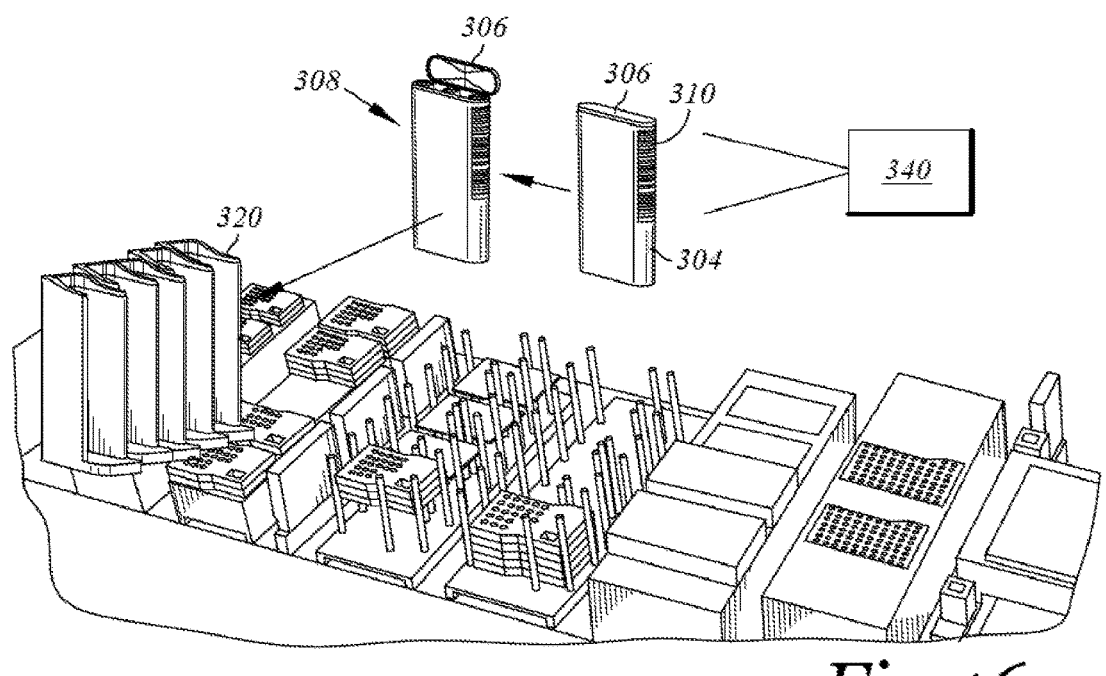
FIG. 16 is a perspective view of a mechanism for opening the lids of containers so the holders in the containers may be removed.
Figure 17:
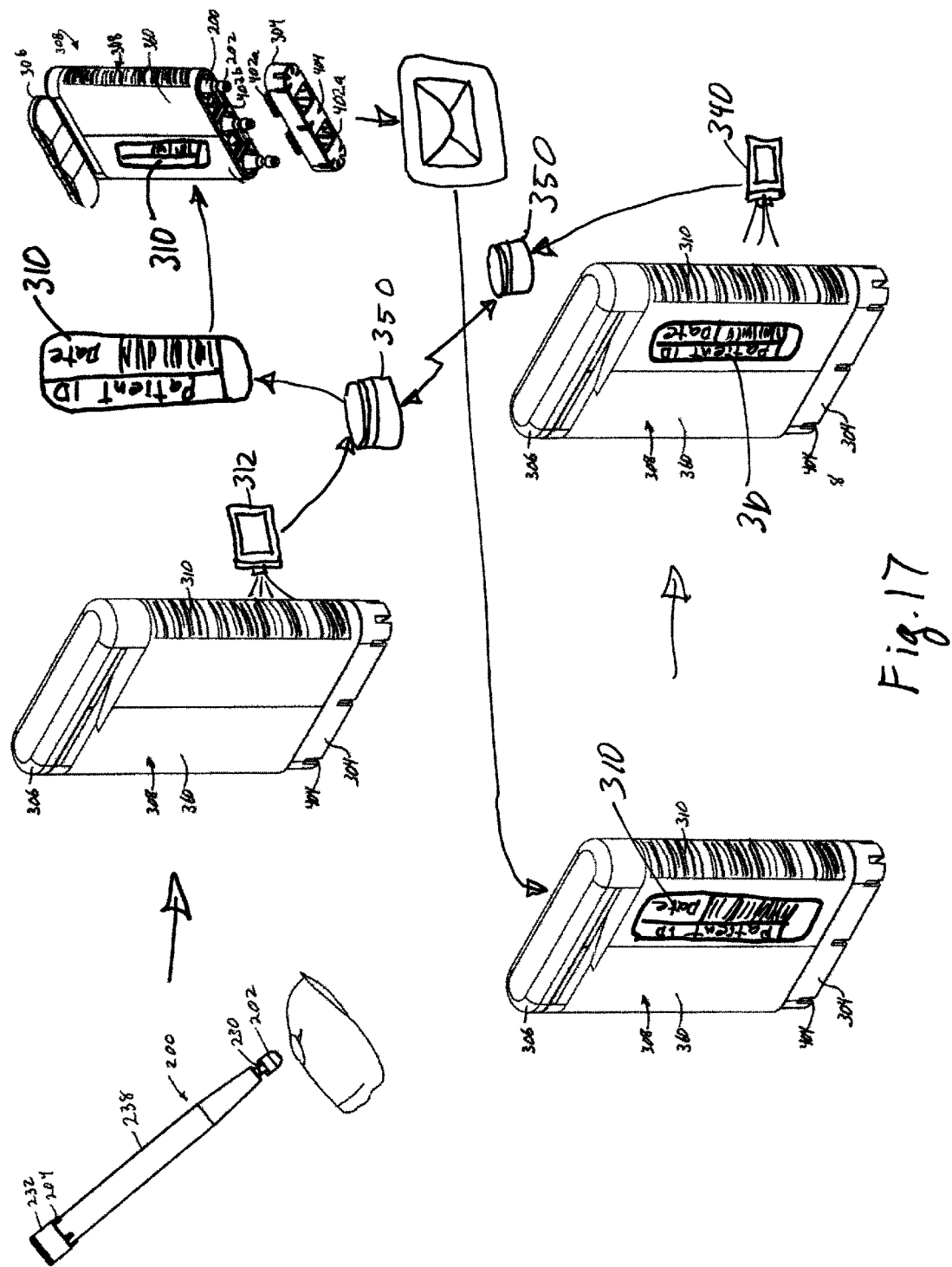
FIG. 17 shows the sequence of events for processing containers of holders.

Referring to FIGS. 15-16, the container 308 has printed indicia 310 on the container. The printed indicia 310 may contain some or all of the information of printed indicia 300 or additional information such as information relating to tracking the container. The information contained in printed indicia 310 advantageously information uniquely associated with the container 208, such as a serial number in any numerical, alphabetic or alphanumerical format. The holder 200 thus has printed indicia 300 containing information on the patient or sample as well as the holder 200, while the container 308 has printed indicia 310 containing information on the container 308, the holder 200, the sample or patient, or any combination thereof. Advantageously the container printed indicia 310 is located on an end or spine of the container 308 and contains a non-repeating, 12-digit serial number in Code 128 barcode format, in human readable form, or both. The container printed indicia 310 is read, recorded, scanned by user scanner 312 or otherwise acquired and transferred to a processor that associates the relevant information with each holder or sample in the container. The container 308 is then sent to a facility for further processing, preferably by mail, courier, UPS, or various other forms of parcel delivery.

The acquisition of a fluid sample and subsequent placement of the absorbent tip 202 in the container 308, drying, labeling and the initiation of shipping—are advantageously performed by one or more persons collecting the samples. The absorption of a predetermined volume by tip 202 and the configuration of the holder 200 and container 208 allows a user with minimal training to adequately collect, prepare (e.g., dry) and ship a sample.

Referring to FIG. 16, the container 308 is received at a processing location and opened manually or opened by an automated opening device 320, before or after being placed in a handling tray 330. The handling tray is configured to receive at least one, and preferably to receive plurality of containers 308 so as to position the holders 200 in each container 308 at a predetermined location. That predetermined location positions the printed indicia 300 or 310 at a location to be read by a reading device or human, or positions the holders 200 to be engaged by an automated mechanism to remove the holders 200 from the containers 308, or any combination of these. The information in the printed indicia 300, 310 is acquired by any of various facility scanners 340 using optical sensors, electronic sensors, magnetic sensors or combinations thereof that "read" or otherwise acquire information from the printed indicia 300, 310 and transfer that information to a facility-processor 350 that is preferably based at the processing facility. The automated mechanism removing the holders from the container 308 places the holder in a well 200 of holder rack 210. The information in printed indicia 300, 310 is compared to ensure the correct sample was received and is being processed. As needed, one or more scanners, including facility scanner 340 identifies each holder 200 and the facility-processor 350 keeps track of which holding rack 210 the holder is placed into, and which opening 206 in the rack the holder is placed into, preferably by correlating with the printed indicia 250 on the rack (e.g., E12).

Referring to FIG. 16, there is advantageously disclosed a method of acquiring and processing the collection and/or processing of fluid samples. The user acquires a sample by contacting the absorbent tip 202 with the fluid sample to be collected. The tip 202 absorbs a predetermined volume of fluid in a predetermined amount of time. The user dries the tip 202 before or after inserting the holder 200 into the container 308. The holder has printed indicia 300 and the container has printed indicia 310, with at least some of the information in the indicia 300, 310 being the same. At least some of the information in the indicia 300, 310 is scanned by a user scanner 312 and either stored to transmitted to the processing facility, such as processing facility processor 350. The user encloses the holder 200 in container 208 and ships the closed container to the processing facility. The processing facility acquires the information from the indicia 310 before or after opening the container 308, and acquires the information in indicia 300 that is not contained in indicia 310 after opening the container 300 and reading indicia 300. Advantageously the information in indicia 300, 310 is acquired by processing facility scanner(s) 340. After the container 308 is opened at the processing facility a mechanism removes the holders from the container and places them in the holding rack 210, with facility scanners 340 and facility processor 340 keeping track of the holders and racks 200 in which the holders are placed, and correlating the information in indicia 300, 310 to track the handling of each sample associated with each holder 200. The holding rack 210 is placed on one or more well plates 220 and the samples in each holder are processed according to the particular processing sequence associated with the nature of the sample and analysis to be performed.

The processing steps are performed on selected absorbent tips 202 of each holder in the same rack. Typically, one or two samples are analyzed and others held in reserve for backup samples in case an error occurs, or retesting is requested, with the remaining samples being stored for archival or future reference or studies. Thus, some or all of the holders 200 in a particular rack may be analyzed.

Typically the absorbent tips are placed in contact with fluid 228 in a single well 222 to extract the sample from the tip 202, after which the holders are removed from the well plate 220, removed from the rack 210 and discarded. The facility processor 340 tracks subsequent processing of the extraction fluid 228 and the extracted sample n that fluid 228. The results of the further processing or analysis are correlated with the information from indicia 300, 310 and transmitted to appropriate locations, including transmittal to the user who collected the sample or the employer of that user, or the processor 350 of that user.

Figure 18A:
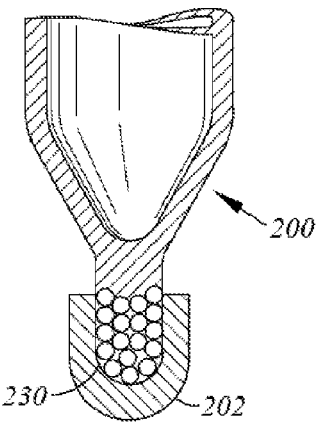
FIGS. 18a-18e are cross sectional views of alternative holder tips providing differing amounts of fluid flow through the tip of the holder.
Figure 18B:
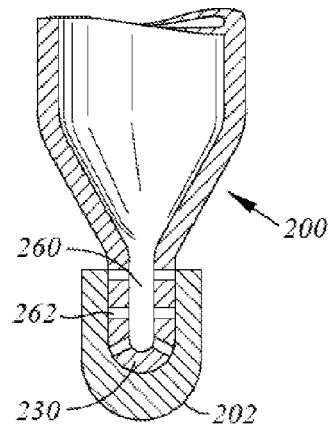
Figure 18C:
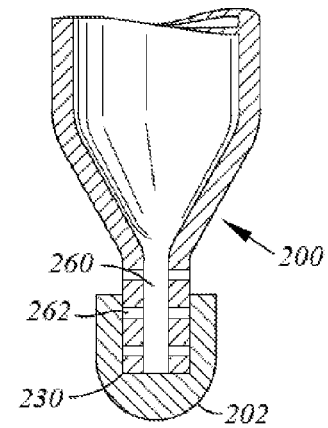
Figure 18D:
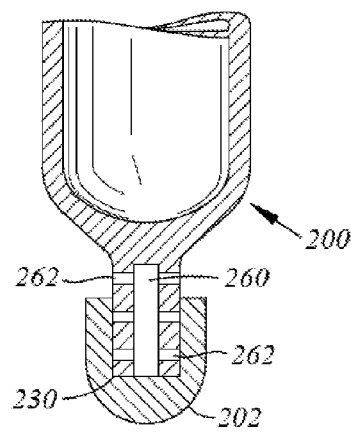
Figure 18E:
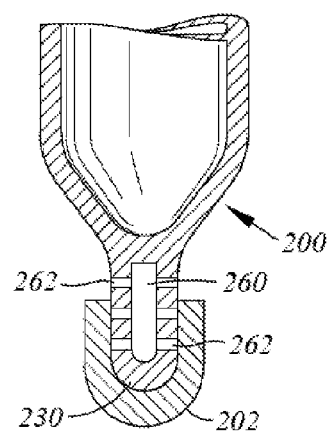
Figure 19A:
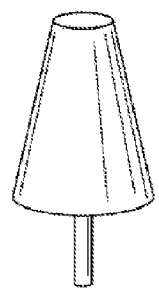
FIGS. 19a-19i show variations in the configurations of absorbent tips.
Figure 19B:
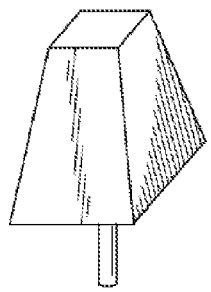
Figure 19C:
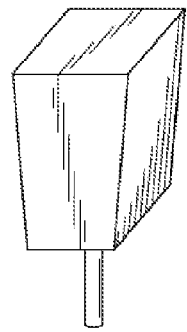
Figure 19D:
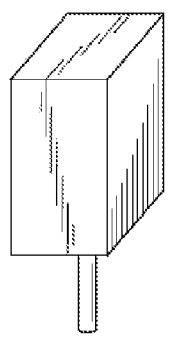
Figure 19E:
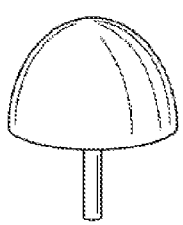
Figure 19F:
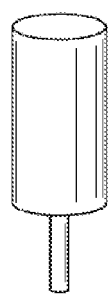
Figure 19G:
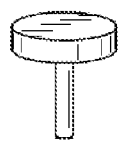
Figure 19H:
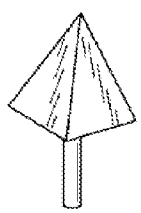
Figure 19I:
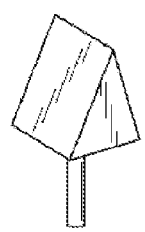

Referring to FIGS. 18a-18d, the projecting tip 230 is preferably of a solid material (FIG. 2c) to provide structural support but need not be so. The tip 230 may be of a permeable material, such as porous sintered plastics as in FIG. 18a. Alternatively, as shown in FIG. 18b-18d, the tip 230 may be tubular with a hollow central cavity extending 260 along a length of the tip 230 having a plurality of side openings 262 extending through the side wall of the tube to form a fluid path from the inside to the outside of the tubular tip 230. The location and configuration of the openings 260, 262 must be considered in determining the volume of fluid that the absorbent tip 202 is to absorb.

If a through-flow design is used on the holder tip 230, then a cylindrical shaped central cavity 260 is preferred, with radial openings 262. The hollow central cavity 260 advantageously has an upper end opening to the interior of the holder 200 (FIGS. 18b, 18c). The lower or distal end of the central cavity 260 may extend to the very distal end of the tip 230 (FIGS. 18c, 18d), or it may end before the distal end (FIGS. 18b, 18d) so as to form a cavity 260 having a closed distal end, with or without a closed upper end. The cavity 260 and side openings 262 are provided to facilitate flow of extraction fluid through the absorbent tip 202 that is connected to the tip 230. Depending on the selected flow path of the extraction fluid, one or several side openings 262 may be formed above the absorbent tip 202 and in fluid communication with the central cavity 260 as in FIGS. 18c-18d. As used herein, several means at between least two and twelve, preferably from two to ten, and more preferably from two to five. Side openings 262 may be placed in the lower end of the holder 200 (FIG. 18c). Thus, extraction fluid could flow from the lower end of the holder 200 through the central cavity 260 and out the side openings and an open end of the central cavity 260, or through side openings 262 and out an open lower end of the central cavity, or through one side opening 262 and out of a different side openings 262 after passing through a closed ended central cavity 260. Advantageously, the bottom or most distal end of the central cavity 260 is either open or is in a draining fluid communication with a side opening 262 so that little or no extraction fluid is trapped in the bottom of the central cavity 260.

The central opening 260 and side openings 262 may be formed when the holder 200 is molded, or the openings may be formed by removing material after the holder is formed as by cutting or drilling material out, with the bottom of the tip 230 being plugged if it is desired to form a close-ended cavity 260. As the shape and location of the openings 262 may affect the fluid absorption by the tip 202, the location and configuration of the openings 260, 262 must be considered in the design of the absorbent tip 202.

Figure 24:
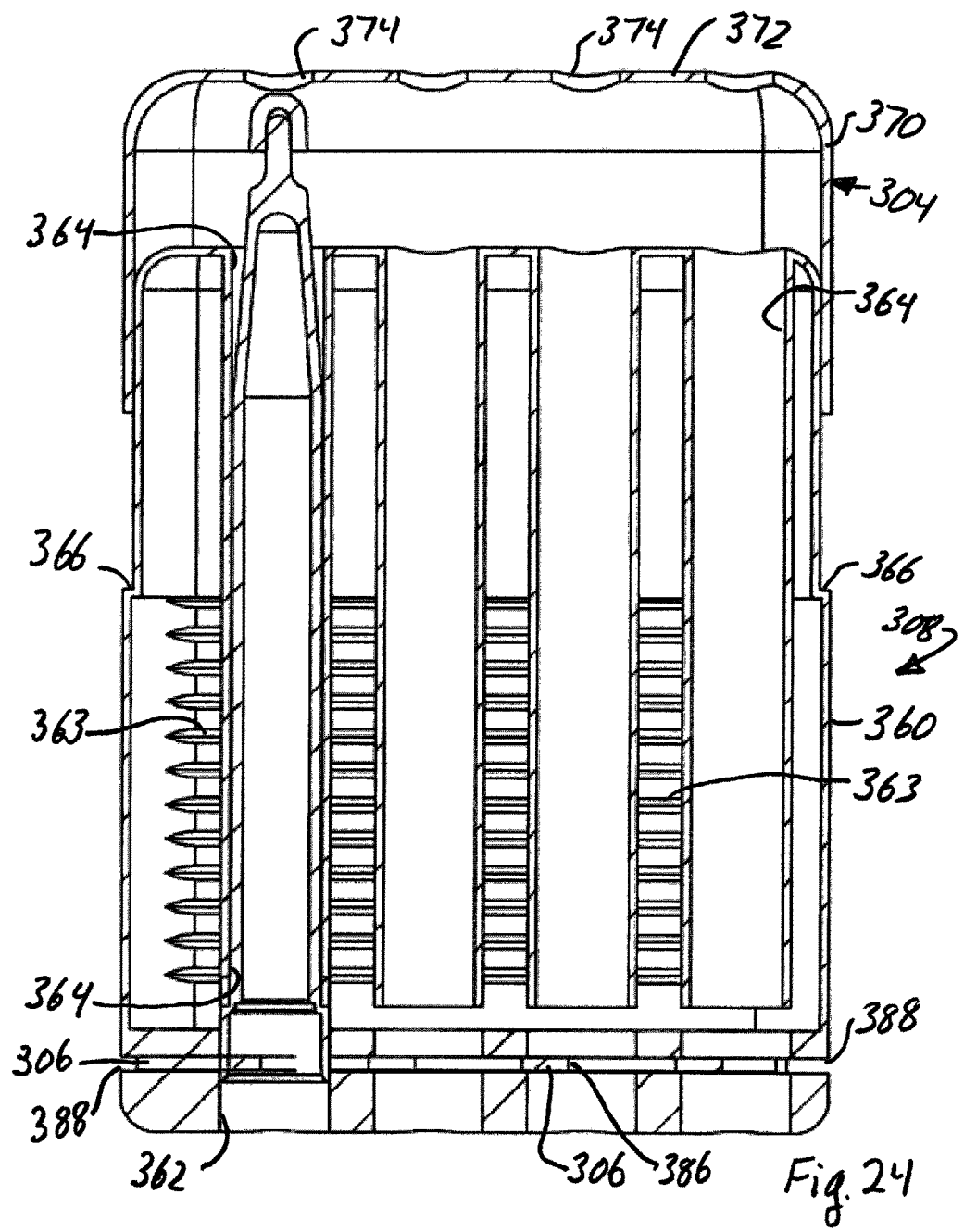
FIG. 24 is a sectional view of the cartridge of FIG. 21 with one holder therein.

Referring to FIGS. 14 and 20-24, the cartridge or container 308 advantageously comprises a generally rectangular container preferably with rounded ends and having a frame therein configured to releasably retain several holders, preferably with the absorbent tips 202 inside or outside the body of the container. The depicted container 308 has a body portion 360 with a first, insertion end with a separate opening 362 for each of four holders 200. Each holder 200 may fit inside a separate cylindrical tube 364 (FIG. 24) associated with each opening 362. The tubes may be contacting each other or spaced apart by braces 363 extending between the tubes and/or adjacent parts of the body 360 (FIG. 24). The tubes 364 and any internal braces 363 comprise the frame for releasably retaining the holders 200. In this embodiment the frame is connected in a fixed position relative to the container body 360, with the distal absorbent tips 202 extending beyond the body 360 when the holders are in the retained position for transport in the container 308. The length of the tube 364 is preferably shorter than the length of the holder 200 and its absorbent tip 202 so the absorbent tip extends beyond the end of the tube when the holder is restrained in the corresponding or mating tube 264.

The relative position of the tube 264 and holder 200 is preferably determined by ribs 204 on the holder contacting the top of the tube 364 into which the holder is inserted, or by slightly tapering the tubes 364 relative to the holder 200 so the holders are wedged into position by a friction fit. Other relative positioning mechanisms could be used, including motion stops on at least one of the tube 364, holder 360 or tube 364. These positioning mechanisms can thus establish the relative axial position of the holder and tube in the container body 360.

As seen in FIGS. 20-22 and 24, the tubes 364 may open onto the distal end of the body 360 so that the holders 200 and the absorbent tips 202 extend beyond the end of container body 360. The container cap 304 fits onto the end of the container body 360 opposite the openings 362. The cap 304 is shaped to conform to the shape of the container body 360 with which the cap mates during use. The cap 304 is thus generally rectangular as the container body 360 is generally rectangular. The cap 304 has a generally U-shaped cross-section so the side walls 368 and end walls 370 of the cap fit over the mating side walls and end walls of the body 360. A motion stop 366 is provided on one or both of the cap 304 and container body 360. As best seen in FIG. 24, the mating side wall and end wall of the container body 360 is slightly recessed inward to form cap stop 366. The distal end of the body 360 is slightly recessed and abuts the edges of the sidewalls and end walls of the cap 204 when the cap is in its fully seated position abutting the stop 366. The cap 304 has a top with openings or holes 374 aligned with tubes 364 to allow the absorbent tips 202 to pass through the openings 374. In the fully seated or fully engaged position at least the absorbent tips 202 and preferably a portion of the holders 200 extend through the openings 374 of the cap 304 to expose the absorbent tips to air for drying.

As best seen in FIGS. 20-22, four holders 200 and absorbent tips 202 may be substantially enclosed inside the generally rectangular container 308 and resting on the end of the container opposite the absorbent tips 202 for drying, or resting on the side of the container for drying. The container 308 positions the absorbent tips away from the surface on which the container is placed for drying. Orienting the container 308 and holders vertical is preferred for drying and ease of handling. The holders 200 are advantageously aligned in a straight row, for ease of handling.

As best seen in FIG. 24, the cap 204 may be moved slightly away from the body 360 a distance sufficient to bring the distal end of absorbent tips 202 within the cap 304, with the cap being connected at that location. By enclosing the absorbent tips 202 inside the cap 304, the cap and body 360 form an enclosed shipping container 308 that may protect the absorbent tip 202 from contact for transporting the holders and the dried samples. The cap 304 thus has two positions, a first, drying position and a second, shipping position. The drying position has the absorbent tips 202 and absorbed samples held in the container 308 but extending of the container so the absorbent tips 202 are fully exposed to air on all sides of the absorbent tip. The second position has the cap enclosing the absorbent tips to protect them from contacting the cap 304 during shipment. The container of FIGS. 14 and 20-24 is shown as configured for four holders 200, but the number can vary. Preferably though, the container is configured to receive several holders 200, preferably 10 or fewer and more preferably 5 or fewer, always holding at least one. The same applies for the other containers described herein. The openings 374 in the cap allow the dried absorbent tips to remain dry by circulating air during transport or at least by providing a ventilated container.

As seen in FIGS. 14 and 22, part of the side wall 368 may be separated by parallel separation lines to form a living-hinge, spring latch 380, with the distal end of the spring latch releasably engaging a protrusion on the container body 360 to hold the cap 304 in position relative to the body 360, preferably holding the cap in the second, enclosed position for transportation.

Referring to FIGS. 14 and 20-23, the body 360 and cap 304 advantageously have gripping surfaces 382. The gripping surfaces 382 may be on one or both sides or ends of the body 360 or cap 304. The gripping surfaces 382 are shown as being on the spring latch 380 of the cap 304. The gripping surfaces may comprise ridges as on the cap as shown in FIG. 23, or recesses or grooves as depicted on the body 360 in FIGS. 20-22, or other textured or roughened surfaces to make it easier to pick up and manipulate a part with robotic manipulators or by hand. Advantageously, the gripping surfaces 382 are on at least one and preferably on both opposing, generally parallel surfaces of the body portion 360 or cap 204.

Referring to FIGS. 14 and 24, the sliding lid 306 takes the form of an elongated plate with holes or openings 386 sized and located to correspond with the location of the holders 200 that are placed in the container 308 during use. The openings 305 are spaced apart in the elongated plate that forms the sliding lid. The plate is thin and flat with the opening 305 spaced along a length of the plate a distance corresponding to that of the tubes 364. The openings 386 are large enough to allow the holders 200 to pass through the openings. The plate is sized to fit through a slot 388 in at least one and preferably both ends of the container adjacent openings 362. The lid 306 slides in the slot across the width of the container body 360. In a first position the lid 306 has openings 386 aligned with the tubes 364 so the holders 200 may be inserted though the lid and into the tubes. In a second position, the lid 306 is slid so that the parts of the plate or lid between the openings 386 extend over part of the path the holders 200 travel when being inserted into the tubes 364 so the holders are restrained from backing out of the tubes. Moreover, the lid 306 may be shorter than the corresponding dimension between the slots 388 so that once the lid is inserted into the slot after the holders are inserted, it is difficult to remove the lid, thus providing a lock, or a lid that is at least very difficult to remove or open.

As seen in FIG. 14, the plate forming the elongated lid 306 has one elongated end 390 with no hole in it to provide a good gripping surface for a user's fingers to grip. The opposing end terminates in the middle of one of the openings 386 so the opposing end as a semi-circular recess in the end. By selecting length of the sliding lid 306 to be less than the distance between the slots 388 on opposing ends of the container body 360, the lid 306 can be positioned so the openings 386 align with the openings to the tubes 364, and the last opening aligns with half of the last tube but does not block passage of a holder through that half-spherical opening—all while leaving enough the elongated end 390 to manually manipulate. When the holders are through the openings 386 and the heads 232 are past the bottom of the sliding lid 306 then a user can push the elongated end 390 completely into the slot 388 to misalign the openings 386 from the tubes 364 and thus the sliding lid blocks removal of the holders past the sliding lid. Since the slots 306 are too small for a person's fingers the holders are locked inside the container body 360. It may be possible to push the sliding lid 306 out with a paper clip or other flat or thin tool, but for practical purposes the holders are locked inside the container body and the sliding lid 306 is releasably locked inside the container body.

Referring to FIGS. 25-29, a further embodiment of a container 308 is disclosed in which several holders 200 are releasably retained in an immovable frame in a container 308. The depicted container 308 is configured for receiving three holders 200 and their associated absorbent tips 202 and any sample contained therein, but the number can vary. Preferably the container releasably receives several holders 200. As with the other containers describe herein, the containers and probes are shipped to a user and returned with a dried sample in the absorbent tip. The depicted container 308 is generally rectangular with rounded ends with printed container indicia 310 provided on at least one end or side wall of the container and preferably on two opposing ends or two opposing side walls of the container. The container 308 has first end with a lid 306 that is connected along one side wall of the container with a hinge, preferably with a living hinge. The lid 306 in this embodiment is configured to fit over and cover the elongated opening of the container, so the lid has depending sidewalls. Advantageously, the depending flange or skirt on the lid 306 forms a friction fit with the mating portion of the container body 366 to keep the lid closed. Preferably the lid 306 contacts the proximal end 323 of the holders 200 to keep the holders snuggle positioned in the container 308. The holders 200 are in tubes 364 described earlier and that description is not repeated. The container body 360 is preferably short enough so that the distal end of the holders and absorbent tips extend beyond the body 360. That allows the container to be laid on its side or stood upright on the closed lid 306 to allow complete access to the absorbent tips 202 for drying as described herein.

The end of the container 308 opposite the lid 306 is configured to receive cap 304 to enclose the distal ends of the holders 200 and absorbent tips 202. The cap has at least one and preferably a plurality of leaf springs or spring latches 400*a* configured to mate with corresponding latches 400*b* on the mating end of the container body 360. The spring latches 400*a* are shown as a square enclosure of sidewalls walls slit down the middle of each wall and preferably slit at each corner to provide a number of resilient, leaf springs that may move toward and away from the square configuration. An outward extending flange on the end of the latches 400*a* engages corresponding surfaces in the container body during use. Mating latch recesses 400*b* are formed in the mating end of the container body 360 and located between the extending holders 200 and their tips 202. Outwardly extending flanges arranged in a square configuration corresponding to spring latches 400*a*, advantageously form the latch recesses 400*b*.

During use, the springs latches 400*a* resiliently engage with the latch recesses 400*b* (FIG. 25) to hold the parts together in a snap lock fit. As seen in FIGS. 25, 28, the latches 400*a* are accessible from the exterior of the cap 304. But once mated with the container body 360, the cap cannot be easily removed except by breaking it or by using a tool designed to release the latched parts 400*a*, 400*b*. While a square arrangement of latches 402 is used, the number and configuration may vary.

The cap 304 also advantageously has optional, but preferred, vent openings 404 in the cap. These are similar to the ventilation provided by openings 374 in the prior cap. The latch parts 400*a*, 400*b* also provide ventilation for the movement of air when the cap 304 is on the container body 360 to enclose the absorbent tips 202. The cap is configured so it does not contact the absorbent tips 202, and the container body is configured to hold the absorbent tips in a desired position with high accuracy as described herein.

Referring to FIGS. 30-34, a further embodiment of the container 308 is shown which has holders 200 in a movable frame configured to slide along a length of the container to extend and retract the holders 200 and expose the absorbent tips to air for drying. The depicted configuration has four holders 200 and the number of holders can vary there are preferably only several holders in each container 308. The container 308 has a hinged lid 306 with an internal boss configured to fit inside the mating opening of the container body 360 and an outwardly extending flange both of which help provide a close fitting end to the container body 360. FIGS. 30 and 32-33 show a rectangular lid mating with a generally rectangular container body 360 having with rounded ends, but the lid shapes preferably match the opening shape as in FIG. 32. The lid 306 has a recess 410 along one edge of the lid with the recess configured to releasably engage a latch 412 (FIG. 34) on the container to hold the lid in the closed position until the lid is intentionally unlatched. Preferably a tool is required to release the latch 412. The latch 412 is preferably a rotating latch with a hook that engages the edge of the recess 410 to hold the lid in the closed position.

The container is generally rectangular as describe above and has a frame 418 with a proximal surface 420 configured to engage the ribs 204 on the holders 200 to position the holders relative to the frame. The frame has a plurality of openings in the proximal surface 420 with a holder 200 extending through those openings. The frame engages a sufficient length of the body of the holder 200 to accurately position the holder relative to the frame 418. The frame may use the tubes 364 of FIG. 24 to position the holders. The frame 418 is connected to a post that extends through slot 422 in the wall of container body 360 with knob 424 on an outside of the container body also connected to the post so that sliding the knob 424 along a length of the container body 360 also moves the connected frame 418 and the holders 200 held by that frame.

The distal end of the container 308 adjacent the absorbent tips 202 during use, has a plurality of openings 426 to allow the absorbent tips to pass through the openings and be extended outside the body 366 of the container. The openings 426 are shown as a single elongated opening with undulating sides.

In operation, the holders 200 are inserted through open lid 306 into the frame 418 inside the container 308. The frame is preferably in a first, retracted position in which the holders are located entirely within the container body 360. The ribs 204 may contact the surface 420 to align the holders, or the frame may have other alignment features to align the holders and maintain the position of the holders during use and transport. The frame maintains the position of the holders so the absorbent tip of each holder does not contact any part of the container during insertion and use, as is the case with the other containers described herein. For drying, the knob 424 is slid from a first, retracted position to a second, extended position to move the connected frame and holders to the second, extended position in which the absorbent tips are located outside, and preferably entirely outside, the container body 360 for drying. The frame 418 advantageously has guides or a cam and follower to direct the movement of the frame along a preferably straight axis as the frame and holders are extended and retraced. Advantageously, a portion of frame 418 rests in is moves along a rectangular recess having straight, longitudinal sides formed by a correspondingly raised, rectangular surface 428 in the side wall of the container body 360. After drying or as otherwise desired the knob is moved to the retracted position to bring the absorbent tips 202 within the enclosure of the body 360 of the container.

By using a retractable frame 418 the need for a cap is eliminated. The sliding mechanism to advance and retract the frame and holders is of simple construction.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The above description is given by way of example, and not limitation. Given the above disclosure, one skilled in the art could devise variations that are within the scope and spirit of the invention, including various ways of tracking the printed indicia associated with each holder 200, holder rack 210, well plate 220 or container 308. Further, the various features of this invention can be used alone, or in varying combinations with each other and are not intended to be limited to the specific combination described herein. Moreover, while the above described method and apparatus is preferably used to sample and test human blood, it may be used to sample and test blood from any animal. Moreover, the method and apparatus may be used to sample and test human and animal bodily fluids other than blood, and may further be used to sample and test other fluids suitable for use with the above described methods and apparatus. Thus, the invention is not to be limited by the illustrated embodiments.

What is claimed is:

1. An assembly for collecting and analyzing a sample, the assembly comprising:
a well plate having an outwardly extending ledge around at least a portion of the bottom of the well plate, the outwardly extending ledge having a height h, the well plate having a plurality of wells, each well having a closed bottom and a longitudinal axis parallel to the axis of the other wells; and
a rectangular holding rack configured to engage with the well plate and having four corners, the holding rack comprising:
a top portion with a plurality of slots extending through the top portion and opening onto a top surface of the top portion, the slots being arranged to correspond with the plurality of wells of the well plate, each of the plurality of slots having a longitudinal axis parallel to the axes of the wells of the well plate when the holding rack is engaged with the well plate;
a leg extending downward at each corner, each leg having two side portions each extending toward a different adjacent corner so the two side portions at each corner are substantially perpendicular to each other, each side portion ending at a distance spaced apart from the side portion extending from the adjacent corner; and
a tab on an outer surface of at least one side portion of each leg, the tab extending beyond a bottom of the at least one side portion for a distance less than the height h of the outwardly extending ledge, the tab being offset from a plane of the at least one side portion;
wherein when the holding rack is engaged with the well plate, the legs are configured to nest over the well plate with a lower surface of the side portions abutting the ledge of the well plate and with the tabs restraining lateral movement of the holding rack relative to the well plate.

2. The assembly of claim 1, further comprising at least one holder having a distal end with an absorbent tip and a proximal end with a projection extending outward, the bottom end of the projection on the holder being spaced a distance L from a distal end of the absorbent tip, the holder being sized and configured to be insertable through at least one of the slots of the holding rack and into a well of the well plate when the holding rack is engaged with the well plate, the distance L being selected to position the absorbent tip adjacent the closed bottom of the well when the bottom end of the projection abuts the top surface.

3. The assembly of claim 2, wherein there are at least three projections on the holder.

4. The assembly of claim 2, wherein the length L is within about 90% of the distance from the top surface to the bottom of one of the side portions measured along the longitudinal axis of the at least one holder when inserted into the one of the slots so the projection of the at least one holder abuts the top surface.

5. The assembly of claim 2, wherein the absorbent tip contains a dried sample.

6. The assembly of claim 5, wherein the holder has a first printed indicia thereon containing information relating to the holder and a sample absorbed in the absorbent tip.

7. The assembly of claim 2, wherein the holding rack has a gripping surface on two opposing sides of the rack configured to engage a gripper of an automated device.

8. The assembly of claim 2, wherein the holder has a first printed indicia thereon containing information relating to the holder.

9. The assembly of claim 1, wherein at least one of the plurality of wells contains a fluid selected for processing a sample.

10. The assembly of claim 1, wherein each side portion ends at a distance D spaced apart from the side portion extending from the adjacent corner, the distance D being selected to allow a gripping device to engage the ledge and hold the well plate and rack.

11. The assembly of claim 1, wherein at least one of the plurality of slots has a larger diameter at the top of the slot and a smaller diameter at the bottom of the slot.

12. A kit for collecting and analyzing fluids, comprising:
one or more holders each having a distal end having an absorbent tip thereon,
one or more containers having a plurality of compartments, each compartment configured to releasably receive one of the holders and to maintain the absorbent tip of the received holder from contacting the compartment or another absorbent tip, each container having a cap configured to releasably enclose the absorbent tips;
a well plate having an outwardly extending ledge around at least a portion of the bottom of the well plate, the outwardly extending ledge having a height h, the well plate having a plurality of wells, each well having a closed bottom and a longitudinal axis parallel to the axis of the other wells; and
a holding rack configured to engage with the well plate and having four corners, the holding rack comprising:
a top portion with at least one slot extending through the top portion and opening onto a top surface of the top portion, the at least one slot being sized and configured to receive at least one container;
a leg extending downward at each corner, each leg having two side portions each extending toward a different adjacent corner so the two side portions at each corner are substantially perpendicular to each other, each side portion ending at a distance spaced apart from the side portion extending from the adjacent corner; and
a tab on an outer surface of at least one side portion of each leg, the tab extending beyond a bottom of the at least one side portion for a distance less than the height h of the outwardly extending ledge, the tab being offset from a plane of the at least one side portion;
wherein when the holding rack is engaged with the well plate, the legs are configured to nest over the well plate with a lower surface of the side portions abutting the ledge of the well plate and with the tabs restraining lateral movement of the holding rack relative to the well plate;
wherein when the holding rack is engaged with the well plate and when at least one container is inserted through the slot of the holding rack with the cap released, the absorbent tips of the holders are inserted into a well of the well plate.

13. The kit of claim 12, wherein the one or more containers and the one or more holders are sized and configured to position the absorbent tip of each holder adjacent a bottom end of a well of the well plate when the holding rack is engaged with the well plate, the container is inserted through the slot of the holding rack, and the cap is released.

14. The kit of claim 13, wherein the holding rack has a gripping surface on two opposing sides of the rack with each gripping surface configured to engage a gripper of an automated device.

15. The kit of claim 12, wherein each of the one or more holders has a first printed indicia containing information relating to the holder.

16. The kit of claim 12, wherein each of the one or more containers has a second printed indicia containing information relating to the container.

* * * * *